United States Patent
Amis et al.

(10) Patent No.: US 7,008,446 B1
(45) Date of Patent: Mar. 7, 2006

(54) THERMALLY PLIABLE AND CARBON FIBER STENTS

(76) Inventors: James Peter Amis, 1410 Elva Terr., Encinitas, CA (US) 92024; Hoi Sang U, P.O. Box 1008, Rancho Santa Fe, CA (US) 92067

( * ) Notice: Subject to any disclaimer, the term of this patent is extended or adjusted under 35 U.S.C. 154(b) by 0 days.

(21) Appl. No.: 10/223,568

(22) Filed: Aug. 19, 2002

Related U.S. Application Data

(60) Provisional application No. 60/313,284, filed on Aug. 17, 2001.

(51) Int. Cl.
*A61F 2/06* (2006.01)

(52) U.S. Cl. .................. 623/1.21; 623/1.19
(58) Field of Classification Search .......... 623/1.15, 623/1.18, 1.21, 1.19
See application file for complete search history.

(56) References Cited

U.S. PATENT DOCUMENTS

| | | | | |
|---|---|---|---|---|
| 5,061,275 A | * | 10/1991 | Wallsten et al. | 623/1.22 |
| 5,292,321 A | * | 3/1994 | Lee | 606/28 |
| 5,957,975 A | * | 9/1999 | Lafont et al. | 623/1 |
| 6,245,103 B1 | * | 6/2001 | Stinson | 623/1.22 |
| 6,281,262 B1 | * | 8/2001 | Shikinami | 523/105 |
| 6,500,204 B1 | * | 12/2002 | Igaki | 623/1.18 |
| 6,524,345 B1 | | 2/2003 | Välimaa et al. | |
| 6,607,553 B1 | * | 8/2003 | Healy et al. | 623/1.11 |
| 2002/0098278 A1 | * | 7/2002 | Bates et al. | 427/2.1 |

* cited by examiner

*Primary Examiner*—Bruce E. Snow
(74) *Attorney, Agent, or Firm*—Stout, Uxa, Buyan & Mullins, LLP

(57) ABSTRACT

A prosthesis for insertion into a body passage is disclosed. The prosthesis includes a plastic or polymer base material which is compatible with living tissue and which possesses a memory of a predetermined configuration. The base material further has a glass transition temperature at which the prosthesis can be molded intravascularly from the predetermined configuration to a larger-radius implant configuration, which is sized and shaped to conform to an internal anatomy of the body passage to expand a narrow segment of or to occlude an opening of an out pouch of the body passage. The glass transition temperature is greater than a temperature of the body passage so that the prosthesis after being molded can be allowed to cool to the temperature of the body passage.

58 Claims, 10 Drawing Sheets

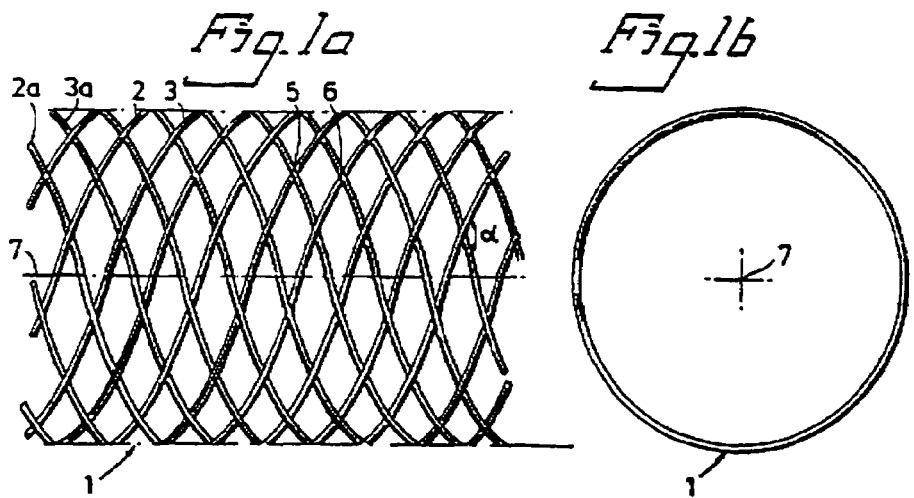
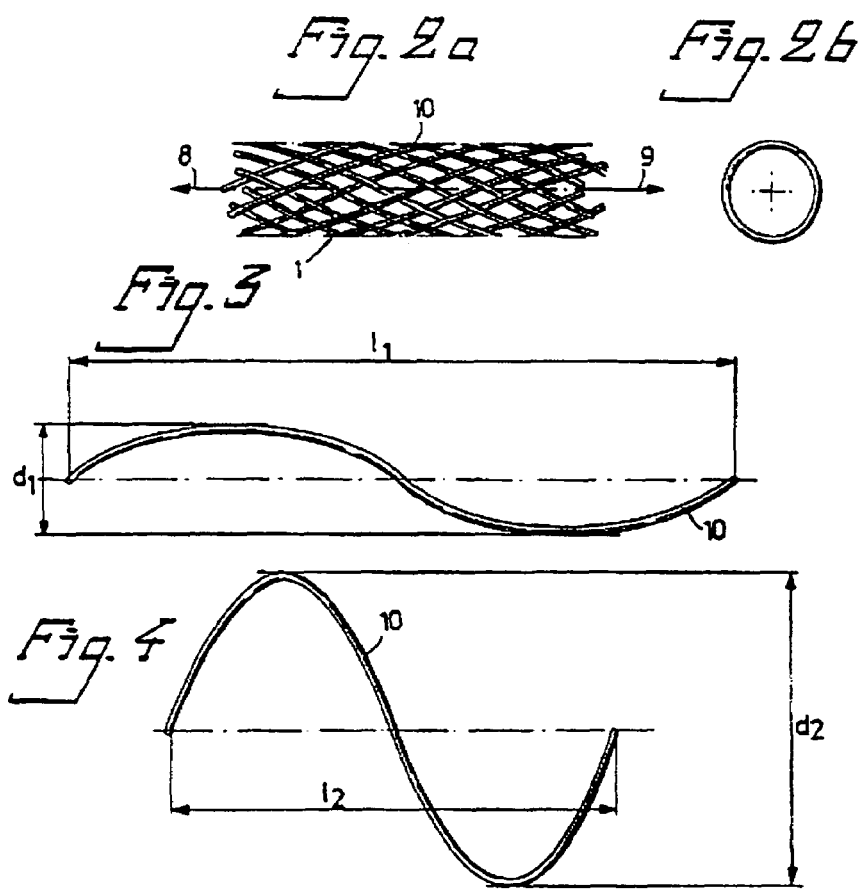

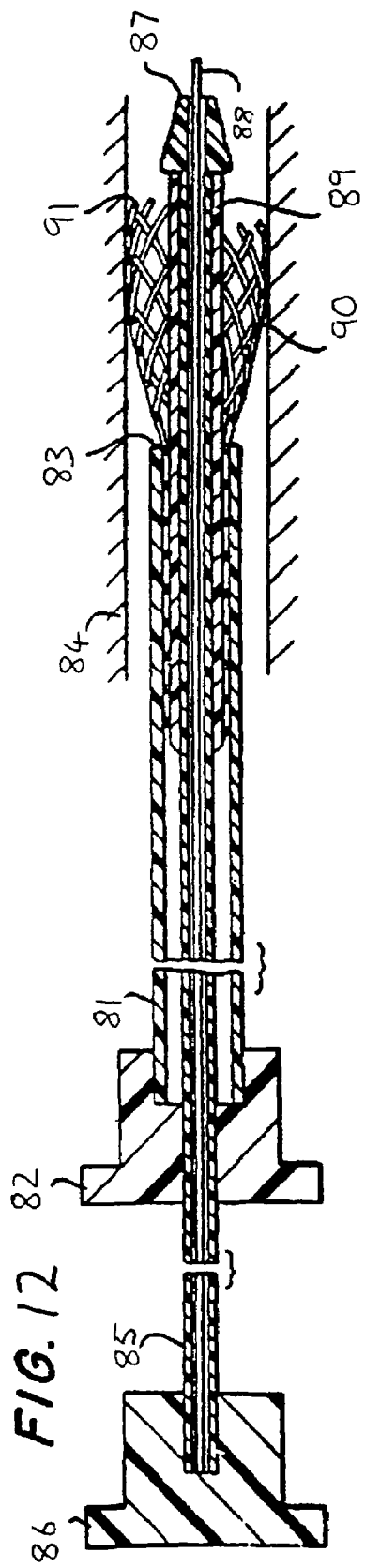
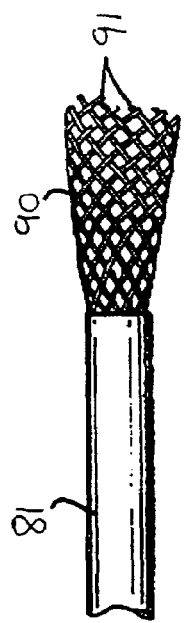
FIG. 12
FIG. 13

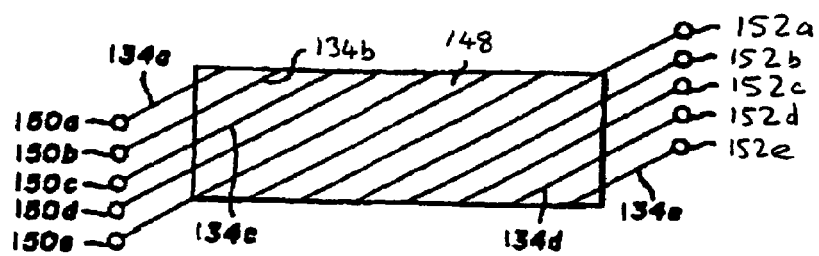
FIG. 26
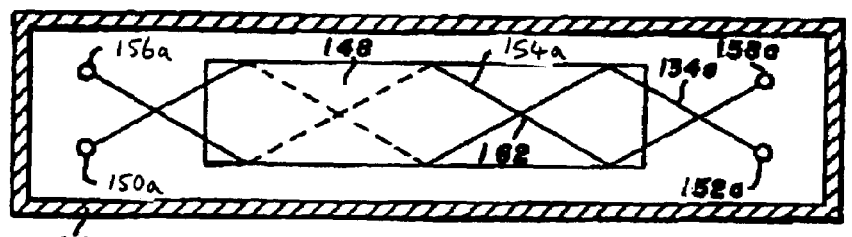
FIG. 27
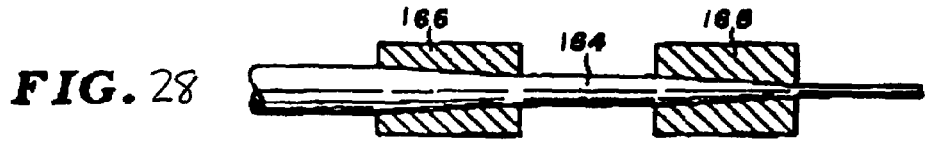
FIG. 28
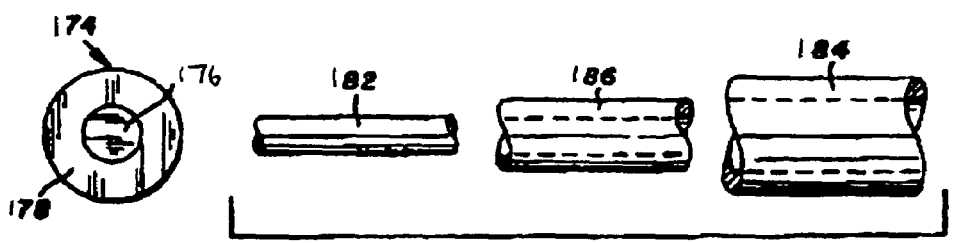
FIG. 29   FIG. 30
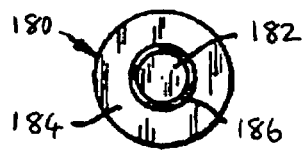   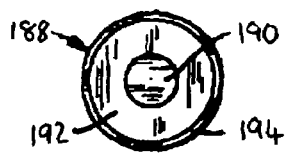
FIG. 31   FIG. 32

THERMALLY PLIABLE AND CARBON FIBER STENTS

This application claims the benefit of U.S. Provisional Application No. 60/313,284, filed Aug. 17, 2001, the entire contents of which are incorporated herein by reference.

BACKGROUND OF THE INVENTION

1. Field of the Invention

The present invention relates generally to medical devices and, more particularly, stents.

2. Description of Related Art

In recent years a number of minimally invasive techniques have been developed to treat occlusive vascular disease, and to repair aneurysms occurring in the circulatory system, vessels, and other organs. In occlusive vascular disease, such as arteriosclerosis, plaque accumulates within a vessel and gradually narrows the vessel to a degree that the vessel can no longer supply an adequate flow of blood. A number of vascular prostheses have been developed to re-expand and retain the patency of such afflicted vessels, for example, after atherectomy or angioplasty.

SUMMARY OF THE INVENTION

Prostheses are disclosed which can be applied within or replace part of for example blood vessels of the body of a living animal or a living human or be placed in some other places which are difficult to access. The prostheses may include a flexible tubular body, the diameter of which can be decreased or increased. The invention is particularly useful, for example, for mechanical transluminal implantation by means of an expanded self-fixating prosthesis for blood vessels, respiratory tracts or the like. By means of a device of the present invention the inner walls of damaged blood vessels or other organs may be lined.

The prostheses of the present invention may be applicable to, for example, surgical and other medicinal techniques, where there may be a need for inserting and expanding a device in for example blood vessels, urinary tracts or other places that are difficult to access which has for its function to support the vessel or tract and which can be left in a position.

The devices according to the present invention can be used also in many medicinal applications and, as examples, there may be mentioned utilization in different types of aneurysm reflected by some form of vessel widening and outpouching, or the opposite, stenosis, which involves constriction of blood vessels. Thus, more specifically, the invention can be used for example to support and keep open vessels of vascular systems, to close pathological vessel abnormalities, to bridge pathological vessel dilatations and ruptures in interior vessel walls or for example to stabilize bronchial tubes and bronchi. The device according to the present invention may also be designed to act as a filter for thrombosis, for example by application in Vena Cava Inferior to prevent the formation of lung emboliae. The invention may be particularly suited to be used as a prosthesis, for example a graft, for application in blood vessels or other tubular organs within the body.

In accordance with one aspect of the present invention, the prostheses are used as or with coronary stent systems for improving coronary luminal diameter in the following: patients with symptomatic ischemic heart disease due to discrete de novo or restenotic native coronary artery lesions (length less than or equal to 25 mm) with reference vessel diameters ranging from 3.0 to 4.0 mm; and treatment of abrupt or threatened closure in patients with failed interventional therapy in lesions less than or equal to 35 mm in length) with reference vessel diameters of 2.5 to 4.0 mm.

The prostheses of the present invention may also be used with therapeutic techniques on the hemodynamic field that include the use of stents for aortic coarctation, secondary aneurysm due to conventional balloon plasty being one of the principal indications. Use of a percutaneous stent in accordance with the present invention can be a fitting therapeutic option for patients who undergo coarctation of aortic angioplasty, develop aneurysm, and are later sent to surgery, with the procedure offering stability to the wall vessel and gradient disappearance. These inventive prosthesis applications are particularly suitable for use in supporting and holding back a dissected arterial lining which can occlude the fluid passageway therethrough.

The prostheses of the present invention may be constructed in a number of stent designs for use in conjunction with minimally invasive approaches for treating vascular disease and other diseases that cause narrowing of body lumens. Stents are generally tubular shaped devices which function to hold open a segment of a blood vessel or other anatomical lumen. These endoprostheses or stents generally consist of an expandable tubular member that contacts and supports the body lumen following a dilatation procedure in which the cause of the narrowing has been treated, for example, by use of a dilatation balloon or atherectomy device. The inventive stents in accordance with the present invention may be used in conjunction with tubular grafts to treat the occurrence of aneurysm, or localized weakening, of a body lumen.

An ideal stent in accordance with the present invention provides a number of mechanical characteristics. For example, it is desirable for the stent to have a small profile and high flexibility when in the contracted state to pass through narrow and tortuous passageways, but to have high radial strength over a range of expanded diameters, with little or no length change when deployed at the desired location. In some applications, such as deployment in the carotid arteries, it is also desirable for the stent to have a high degree of elasticity, so that if it is inadvertently compressed, the stent will re-expand to its originally implanted diameter.

In order to accomplish precise placement of stents in accordance with the present invention, various means can be employed pursuant to the invention to identify the position of the stent within a blood vessel. One means for accomplishing precise placement of a stent is the attachment of radiopaque markers to the stent so that through the use of fluoroscopy or any other imaging technique, the position of the stent within a blood vessel can be identified. Fluoroscopy is the prevailing technique for such visualization, ant it requires radiopaque materials. The traditionally preferred structural materials for prosthesis construction, e.g. stainless steels and cobalt-based alloys, are not highly radiopaque. Consequently, prostheses constructed of these materials do not lend themselves well to fluoroscopy. The radiopaque markers may be created from platinum or a platinum-iridium alloy, or tantalum.

To overcome the problems and limitations associated with stents having conventional radiopaque markers, it would be desirable to create the stent from a carbon fiber or similar material or compound, which preferably does not substantially limit the expansion capabilities of an expandable stent, and provide a means to assess stent length and diameter without obscuring the blood vessel lesion being repaired. Stents composed of carbon fibers are provided in several embodiments of the invention. An intravascular stent composed of carbon fiber or lactic acid polymers may be visualized with magnetic resonance imaging (MRI), fluoroscopy, or any other imaging technique. The stent can be easily imaged during the follow-up of the patient, in order to determine the stability of the location of the stent.

The stent may be also designed to possess memory of selective shapes and sizes, or may be molded intravascularly to conform to the internal anatomy of the vessel, either to expand a narrow segment or to occlude the opening of an out pouch. It should, however, be observed that the invention is not limited to the applications mentioned which must be considered as solely exemplifying.

The present invention has for a purpose to provide a radially expansible and contractile prosthesis whereby drawbacks of known techniques are attenuated or avoided.

The present invention is based on utilization of a prosthesis comprising a flexible tubular body the diameter of which can be changed by axial movement of the ends of the body relative to each other. In a preferred embodiment the body takes a radially expanded position when it is left in an unloaded condition free of external forces in the radial direction. In accordance with one aspect of the present invention, the body of the prosthesis is composed of several individual rigid but flexible thread elements each of which extends in helix configuration with the center line of the body as a common axis. A number of elements have the same direction of winding but are displaced axially relative to each other. The number of elements having the same direction of winding meet under crossing a number of thread elements also axially displaced to each other but having the opposite direction of winding.

In accordance with one embodiment of the present invention there is provided an instrument for the deployment or retraction of a self-expanding braided stent in a body canal, which comprises an elongated tubular outer sleeve having a proximal end and a distal end, an elongated core disposed within the sleeve and movable relative to the sleeve, the core being longer than the sleeve and having a proximal end and a distal end and including a grip member at or near the distal end of the core, the grip member being an integral portion of the core or a sleeve or coating attached around the periphery of the core and being adapted to: (i) releasably hold a self-expanding stent within the outer sleeve, there being sufficient clearance between the grip member and the outer sleeve to accommodate the stent without distortion, (ii) deploy the stent beyond the distal end of the outer sleeve when the outer sleeve is moved in a backward direction relative to the core and (iii) retract the stent back within the outer sleeve when the core is pulled in a backward direction relative to the outer sleeve.

The invention also provides various methods for the deployment of a self-expanding stent in a body canal. In accordance with one method, the stent is pre-located on a grip member of a core within an outer sleeve of an instrument as described above so that the inner surface of the stent is releasably held by the outer contact surface of the grip member, which method comprises passing the instrument into the body canal until it reaches a position for proper placement of the stent and deploying the stent at the position by moving the outer sleeve proximally relative to the core, and withdrawing the instrument when the stent is properly located at the desired position in the body canal.

BRIEF DESCRIPTION OF THE DRAWINGS

FIG. 1A and FIG. 1B show diagrammatically a side view and an end view, respectively, of the flexible tubular body according to the invention;

FIG. 2A and FIG. 2B show the same tubular body as in FIG. 1 but in contracted state;

FIG. 3 and FIG. 4 show one separate thread member of the body, the body being shown in contracted and expanded state, respectively;

FIG. 12 is a side elevation, partly in section, of an instrument according to the invention;

FIG. 13 is an enlarged side elevation of the distal end of an instrument showing a partly deployed stent:

FIGS. 23–27 schematically illustrate a process for manufacturing the stent;

FIG. 28 schematically illustrates a swaging step of an alternative process for manufacturing the stent;

FIG. 29 is an end elevational view of an alternative embodiment filament;

FIG. 30 is an elevational view of several components of an alternative composite filament constructed according to the present invention;

FIG. 31 is an end elevational view of the composite filament formed by the components shown in FIG. 12;

FIG. 32 is an end elevational view of another alternative embodiment composite filament;

DETAILED DESCRIPTION OF THE PRESENTLY PREFERRED EMBODIMENTS

Figure 5:
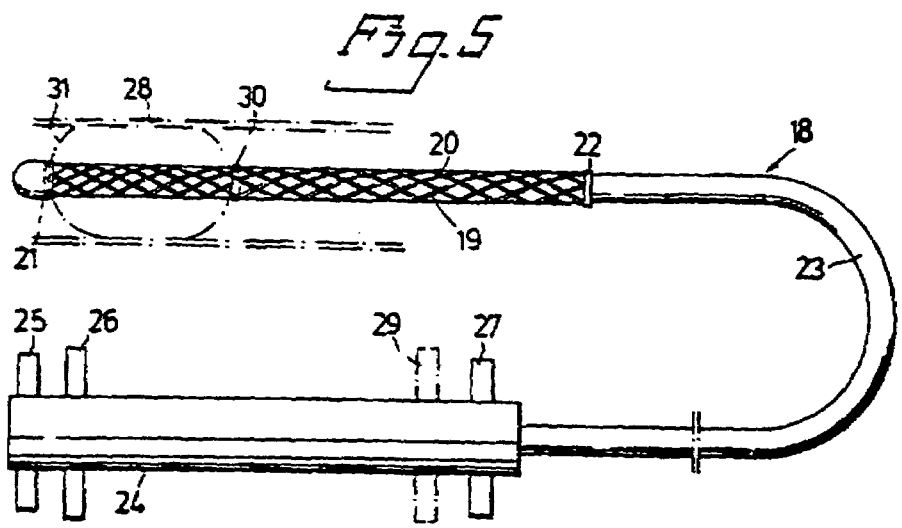
FIG. 5 shows diagrammatically an assembly incorporating the tubular body according to the present invention.

The following disclosure references figures from U.S. Pat. No. 4,655,771, which patent is incorporated herein in its entirety by reference.

A flexible tubular body according to the present invention has been found to be suited for use as a prosthesis for transluminal implantation in blood vessels or other similar organs of the living body. The tubular body is inserted into place in the organism in a contracted state, i.e. with reduced diameter. After the tubular body has been inserted into position it is subjected to expansion and can stay in place in an expanded state by self-fixation if the diameter of the body in unloaded condition is selected somewhat larger than the diameter of the surrounding wall. This construction results in a certain permanent pressure of engagement against the inner wall so as to ensure good fixation.

To obtain the desired function the axially directed angle between crossing elements cam be greater than about 60 degrees, and can in some embodiments be obtuse, i.e. more than about 90 degrees. This state of the body refers to its state in radially unloaded condition.

The crossing thread elements can be arranged in such a manner as to form a sort of braided configuration which may be varied as desired and for example imitate some known type of weaving, for example according to the principle of a plain weave. This can impart to the tubular body the necessary stability. If the number of elements in the flexible tubular body is designated n then n can vary, e.g., from about 10 and up, for example to about 50. The elements of the tubular body can be arranged symmetrically, i.e. the number of elements in each direction of a winding is (n/2). It should be observed that in this connection when referring to the number of elements in the tubular body reference can be had to elements intended to maintain the supporting function of the body. The number of elements n can be selected in accordance with the diameter of the body, the diameter of the element, the material of the element or other factors. Generally, the greater the diameter of the body with a given element material, the more elements should be used to give the necessary stability of the body.

The radially contracted prosthesis, which e.g. is inserted through the wall of the vessel at a distance from the implantation site, will be fixed without the need for conventional removal of the parts of the organ to be replaced. In this manner the blood flow can be maintained even during the implantation which calls for a short period of time. The prosthesis in accordance with certain embodiments need not be stitched to the vessel and already after a few days it can be definitely fixed to the body by means of natural tissue growth.

The flexible tubular body can be brought to expand radially in several ways. It has been found for many reasons that it is preferred that the body has the property of entering into radially expanded and unloaded position by itself. The expanded state of the body may be dependent on the inherent rigidity of the thread elements, but it may also be controlled by elastic strings, bands or membranes, or expandable means such as a balloon catheter which are arranged in connection to the mantle surface of the body and extend axially along same. By their elasticity these strings, bands or membranes result in axial traction of the body, i.e. to bring same to take an expanded state.

An alternative way of imparting properties to the body through which it tends to take a radially expanded position is to attach the elements to each other at the points of crossing thereof in a suitable manner, for example by some form of welding, gluing or the like.

The elements forming the flexible tubular body should be made of a medicinally acceptable material, for example plastic or metal or non-metallic synthetic materials, and can possess certain springiness or rigidity combined with suitable elasticity. The elements may be built up as monofilaments, for example polypropylene, dacron or other suitable plastic or constituted by a composite material. They may also be made from some suitable medicinally acceptable metal.

The free ends of the thread elements of the tubular body can be modified or protected in several ways. The alternative in which no free ends at all are present is the alternative to make the tubular body as a whole of one coherent element. The alternative which is most closely related to that is the case where the free ends of a body resulting from severing a long string are connected with U-shaped members which are attached to the ends of the elements pair-wise in a suitable manner, for example heat welding, gluing or the like. In this manner elements of the same direction of winding or elements of the opposite direction of winding can be attached to each other two and two.

An alternative to these embodiments is to weld together the points of crossing in a ring around the material by electric resistance heating or the like before severing the string, severing then taking place adjacent to and just outside the welding site. The ends then extending outside the welding area may be folded inwardly towards the interior of the body with light plastic deformation, for example through controlled heating. Yet another alternative consists in bending the free ends of the elements to form loops.

In accordance with one embodiment of the present invention, the tubular body is suited for use as a so-called graft. In this case the body may function as a graft namely if it is made of elements of such character as to impart by themselves the desired density and porosity to the body to function as a graft whereby at least a number of the elements may be made of polyfilament materials or the like. The alternative of the elements themselves imparting the desired density to the body is to apply some sort of surface layer to the body, for example of plastic or other suitable material. By applying such surface layer the crossing points may at the same time be fixed as indicated above so as to make the body tend to take an expanded position.

Outside or inside or amalgamated with the body there may also be arranged a separate sleeve or membrane. This can be constituted by a stocking of porous web surrounding the body which can be implanted together with the body. In this case the stocking may, either by stretchability in the web or by overlapping folding or in another manner, for example by being built up in accordance with the same principle as the body from a plurality of thread elements, be adjustable to the body in connection with the expansion thereof. It is also possible to conceive the use of some form of tricot type product or crimped fiber textile. When using such a separate member it is preferred that it is axially fixed relative to the body so as to end up in the right position when applied in a large vessel or the like.

The expansion or contraction of the tubular body can be provided by a device with means which are arranged to elongate or shorten the body. Such means may be designed in many ways, for example so that their construction allows axial movement of the ends of the body relative to each other to reduce or increase the diameter of the body. The device should include gripping members capable of gripping the ends of the body and axially moving the same relative to each other. The gripping members should be arranged so as to be releasable after the application of the body at the desired site so that the device except for the body can be removed from the site. Alternatively, the device may include a flexible tube within which the tubular body is intended to be placed in contracted state, and operating members by means of which the body under expansion thereof can be pushed out of the tube to be applied at the desired site.

In FIGS. 1A and 1B there is shown an exemplary inventive prosthesis in the form of a cylindrical tubular body generally designated 1. As is clear from FIG. 1A the mantle surface of body 1 is formed by a number of individual thread elements 2, 3 etc. and 2a, 3a etc. Of these elements 2, 3 etc. extend in helix configuration axially displaced in relation to each other having the center line 7 of body 1 as a common axis. The other elements 2a, 3a extend in helix configuration in the opposite direction, the elements extending in the two directions crossing each other in the manner indicated in FIG. 1A.

The diameter of a tubular body built up in this manner can be varied if the ends of the body are axially displaced relative to each other in the direction of the center line 7. In FIG. 2A there is illustrated how the tubular body 1 according to FIG. 1A has been given reduced diameter by moving the ends 8, 9 away from each other in the direction of the arrows. FIG. 1B shows the diameter of the tubular body in an expanded state, whereas FIG. 2B shows the diameter of body 1 in contracted state after the ends 8, 9 thereof have been moved away from each other.

FIGS. 3 and 4 show a detail picked from FIGS. 1 and 2, more particularly one single thread element of the tubular body 1 and how its helix configuration will be changed in connection with the change of the length of the tubular body 1.

In FIG. 3 the individual element 10 corresponding to element 10 of FIG. 2A is shown. The diameter of the helix is $d_1$ and the length of the element is $l_1$. In FIG. 4 the same element 10 is shown after the tubular body has been expanded to the state shown in FIG. 1A. The diameter of the helix has now increased and is designated $d_2$, whereas the length has decreased and is designated $l_2$.

Figure 7:
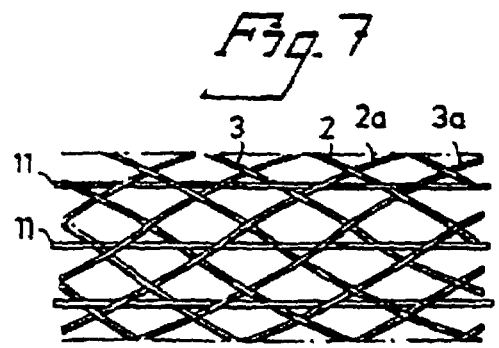
FIG. 7 shows an alternative embodiment of the tubular body.

The tubular body 1 can be expanded in a number of ways. As previously mentioned it is preferred that the body inherently has the property of taking expanded position by itself in unloaded condition. In the present disclosure the expression "expanded position" refers to radial expansion, i.e. a state with a large diameter of body 1. The self-expanding property can be obtained, for example, by providing the body with strings or bands extending parallel and axially with the mantle surface of the body. An example of such embodiment is shown in FIG. 7 where the tubular body 1 is provided with axial strings or bands 11. In such an embodiment wherein strings or bands 11 are used, the strings or bands 11 can be suitably made of an elastic material and can be fixed to the elements of the tubular body 1 in a suitable manner and with the body in expanded state. Now, if the tubular body 1 is axially elongated by moving the two ends thereof from each other the elastic strings or bands 11 will be stretched. After removal of the tensile force from the body 1 the elastic strings or bands 11 will compress the body 1 in an axial direction resulting in a corresponding increase of the diameter of the body. The strings or bands 11 may in a resorbable embodiment comprise a resorbable material so that by changes in temperature thereof they may be brought in and out of a glass transition phase to thereby increase or decrease their lengths. For example, they may be formed so that when they are heated their lengths shorten.

The tubular body 1 can be provided with the same tendency to take expanded position by fixing the elements 2, 3 etc.; 2a, 3a etc. at the crossing points 5, 6 (FIG. 1), as previously mentioned. Another way of providing this effect is to provide for an interior or exterior tubular elastic member, for example of a thin elastomer, which is attached to at least both ends of the tubular body.

In FIG. 5 there is shown a device generally designated 18 to enable insertion of an expandable body, such as the tubular body 20, in contracted and elongated state at the desired site of for example a blood vessel. To the extent compatible, the device may be used with any implant/stent set forth herein. The tubular body 20 surrounds the forward tubular part 19 of apparatus 18 and is attached at both ends thereof to gripping means 21 and 22. The forward tubular part 19 of the apparatus is connected to an operational member 24 through a flexible tubular means 23. By means of operational elements 25, 26 and 27 of the operational member 24 the gripping means 21 and 22 can be controlled in a desired manner.

In FIG. 5 there is shown diagrammatically how apparatus 18 with the contracted tubular body 20 has been inserted into for example a blood vessel which in the figure is shown with dashed lines and designated 28. Operational member 24 is connected with gripping member 22 in such a manner that when the operational means 26 is moved forwardly to position 29 shown with dot and dash lines a gripping member 22 is displaced in a corresponding manner to the dot and dash line position 30. As a result the end of tubular body 20 has been moved from position 22 to position 30, whereas in this case the other end of the body remains in position 21. At the same time the diameter of body 20 has increased and when the end has reached position 30 the body 20 is expanded, i.e. it has been brought into contact with the interior wall of the vessel and has taken dash-dotted line position 31. Since both ends of the tubular body 20 are still held by members 21, 22, body 29 in expanded state takes a balloon-like shape.

Operational means 27 is also connected with the gripping member 22 by means of a part, for example a wire, running in tubular member 23. In this manner gripping member 22 in its position 30 can be maneuvered by axial displacement of operational member 27 to release the end of the body 20. In the same manner maneuvering means 25 which is connected to gripping member 21 can release the forward end of the tubular body from gripping member 21 by axial displacement thereof. The ends of the elastic body 20 are thereby immediately subjected to movements relative to each other to provide for expansion and the prosthesis takes its expanded cylindrical shape in the interior of the blood vessel.

Figure 6:
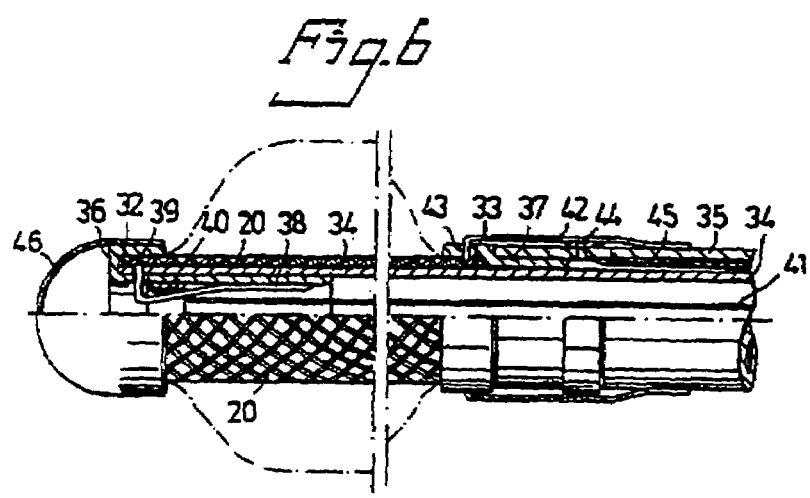
FIG. 6 shows in an enlarged view part of the assembly of FIG. 5.

In FIG. 6 there is shown more in detail and in an enlargement the construction of the forward tubular part 19 of device 18. The tubular body 20 with both its ends 32 and 33 surround a thin-walled flexible tube 34 running inside and concentrically to an outer flexible tube 35, the two tubes of which form the tubular member 23 in FIG. 5. At the front part of the inner tube 34 an annular member 36 is arranged, into which the end 32 of tube 20 is inserted. In a corresponding manner the end 33 of tube 20 is inserted into an annular member 37 which is axially displaceable in relation to the tube 34 surrounded by ring 37. At the front part of tube 34 there is provided an interior gripping member or latch 38. Latch 38 which can comprise spring steel, has a forward pointed part 39 bent under about right angle. This part 39 extends radially outwardly through a hole in tube wall 34. It can move in radial direction under the influence of a ring 40 which is axially movable and arranged inside tube 34. Ring 30 is connected to a wire 41 through which by axial displacement latch 38 can be moved in a radial direction. In FIG. 6 latch 38 is shown in such position that its pointed part 39 has perforated the end 32 of body 20 and thus maintains the end in position.

In the corresponding manner another latch 42 is arranged to hold from outside the end 33 of the tubular body 20 by its pointed part 43. This latch 42 which is attached to the outside of tube 35 can be moved in radial direction by means of a ring 44 arranged about tube 35 and attached to a cable 45 extending between tubes 34 and 35. Cables 44 and 45 are connected to the operational means 25 and 27, respectively, in FIG. 5.

When the attached and axially extended tubular body 20 shall be released from the remaining part of the device after the axial expansion of the body, this takes place by releasing the pointed parts 39, 43 of latches 38 and 42, respectively, from the ends of the tubular body 20 by actuating rings 40 and 44 through operational members 25 and 27 via cables 41 and 45, so as to deflect latches 38 and 42. The ends 32 and 33 of the body 20 will then be released by axial displacement of the tubular part 19 of the apparatus. As is clear from FIG. 6 the front end of the apparatus is protected by a hub or casing 46 attached to ring 36.

Figure 8:
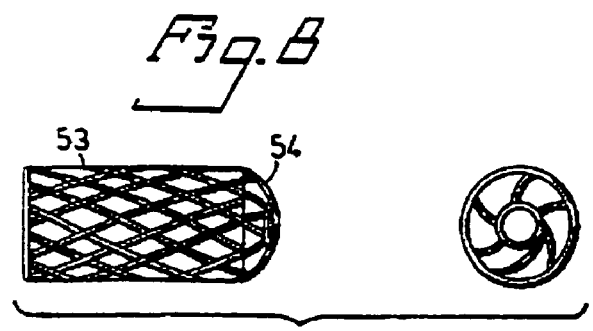
FIG. 8 shows the tubular body designed as a combined graft and filter.

As previously indicated the expansible tubular body finds several applications within surgery. For example, in the embodiment shown in FIG. 1 it can be utilized for supporting vascular walls. In FIG. 8 there is shown a modified embodiment of the flexible tubular body. In this embodiment the body consists of a cylindrical circular part 53 which at one end thereof changes to a diminishing part or end 54 also built up from thread elements. This device has been found to be suitable for use as a sieve or filter to prevent thrombosis. The device shown in FIG. 8 can be applied at the desired location within a blood vessel, for example Vena Cava Inferior, for the purpose of preventing lung emboli.

Figure 9:
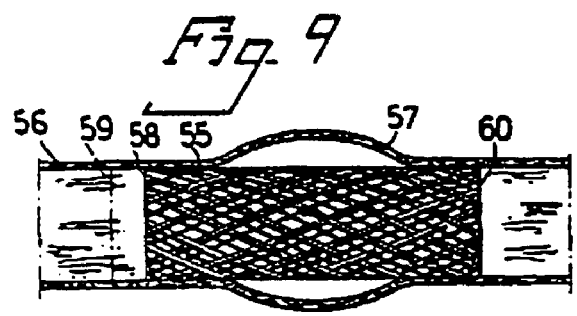
FIG. 9 shows the tubular body used as a graft in connection to aneurism.

In FIG. 9 there is shown a tubular body for use as a graft. In this case body 55 may have a denser or a much denser wall than the embodiment shown in FIGS. 1 and 2. This denser wall can be obtained by weaving an elastic yarn between the supporting thread elements 2, 3 etc.; 2a, 3a etc. of FIG. 1. In this manner a wall having a controlled porosity can be obtained. This tubular body having a more or less porous wall is thus a sort of expansible graft that may have a versatile use.

In the application shown in FIG. 9 the body 55 is implanted into for example an aorta 56 wherein there is an aneurism 57 in the form of a widening of the vascular wall. In view of the fact that the expansible body or graft 55 can be inserted at a distance from the damaged location of an aorta and then located in the middle of the aneurism the latter will be bridged and need not be operatively removed. In FIG. 9 it is also indicated that the aorta is a conical blood vessel. Therefore, the procedure in this case will be that the prosthesis in the form of a graft is inserted with an instrument, for example in accordance with FIG. 5. After being located the graft or body 55 is expanded. In view of the conical configuration of the aorta the surgical techniques will be as follows.

The front end 31 of graft 55 according to FIG. 5 is inserted somewhat further into the aorta than the location it shall take after terminated operation. This position 59 is indicated in FIG. 9 with the dotted line. The other end 22 of the axially extended graft 55 according to FIG. 5 is carried up to the final position corresponding to position 60 of FIG. 9 before the radial expansion. Since this part of the aorta has a somewhat smaller diameter than the diameter in front of the aneurysm as seen upstream in relation thereto the prosthesis cannot expand more than the dimension corresponding to the diameter at end 60. This is, however, alleviated by then moving the other end of the graft 55 by means of the front part of the instrument from position 59 to position 58 so that this end of the graft can expand sufficiently to engage this part of the vascular wall.

Figure 11:
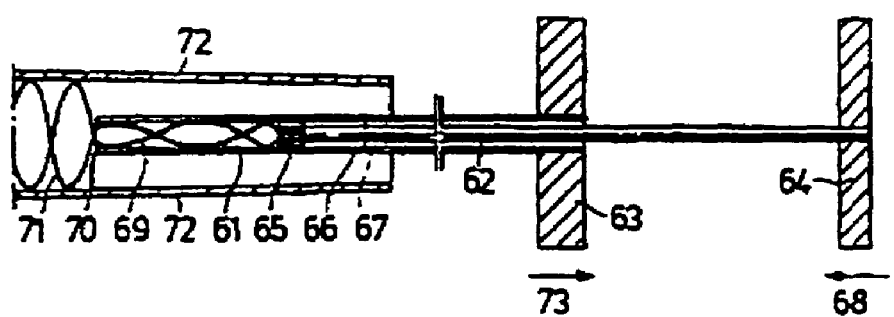
FIG. 11 shows diagrammatically an alternative assembly for manipulating the prosthesis of the invention.

In FIG. 11 there is shown another embodiment of the assembly for use in expanding the tubular body. This assembly constitutes a flexible instrument intended to introduce the tubular body in contracted state into for example a blood vessel and then to expand the body when located therein. The parts of the instrument consist of an outer flexible tube 61 and a concentric also flexible inner tube 62. At one end of the outer tube an operational member 63 is arranged. Another operational member 64 is attached to the free end of inner tube 62. In this manner the inner tube 62 is axially displaceable in relation to the outer tube 61. At the other end of inner tube 62 a piston 65 is attached which when moving runs along the inner wall of outer tube 61.

When the instrument is to be used the tubular expansible body 69 in contracted state is first placed inside tube 61, the inner tube 62 with the piston 65 being located in the rear part 66 of outer tube 61. Dashed lines show the starting position of piston 65 at 67 in FIG. 11. In this manner part of tube 61 is filled with the contracted tubular body 69 in the starting position.

During implantation the flexible tubular part of the device is inserted into the location of a blood vessel intended for implantation. Member 64 is then moved in the direction of arrow 68, the contracted body 69 being pushed out through end 70 of tube 61, the part of the tubular body 69 leaving the tube end 70 expanding until in its expanded position 71, it is brought to engagement with the interior of vascular wall 72. The tubular body 69, 71 is for the sake of simplicity shown in FIG. 11 as two sinus-shaped lines. To the extent that the expanded body 21 comes into engagement with vascular wall 72 moving member 63 in the direction of arrow 73 moves the tube end 70. The piston 65 pushing against one end of the body moves the contracted body 69. Thus, the implantation takes place by simultaneous oppositely directed movements of members 64 and 63, the displacement of member 64 being larger than that of member 63. When the contracted body 69 has been fully removed from the tube 61 the expansion is terminated and the instrument can be removed from the location of the operation.

The embodiment according to FIG. 11 is suitable for implantation of helices with very small diameters. As an example a tubular expansible body may comprise crossing thread elements, the contracted diameter of the body being only 2 mms and the expanded diameter 6 mms. It is also fully conceivable to implant expanded bodies with even smaller diameters. The instrument according to FIG. 11 may also advantageously be used for implantation of bodies in the form of grafts of a very large diameter.

In implantation of long bodies it is conceivable that the resistance in displacing the same in tube 61 becomes too high. In this case it may be suitable to replace piston 65 at the front end of tube 62 with movable jaws or latches which operate in such a manner that when tube 62 is brought forward in the direction of arrow 68 the latches engage the inner side of body 69, the body being brought forward. When tube 62 is brought back in the direction of arrow 73 the latches are released. In this manner a pump-like motion of tube 62 can move body 69 forwardly.

Many embodiments of the different members shown in FIG. 11 are, of course, conceivable. Thus, it is possible for example to simplify implantation for the surgeon by controlling the relative motion between members 63 and 64 in a mechanical manner.

The expansible body should possess certain elastic properties in order to enable successful implantation. For example, when the body is inserted to keep blood vessels open or is implanted as a blood vessel prosthesis it should in accordance with one aspect of the present invention have elastic properties which are as similar as possible to those of the blood vessel of the living body. The body should also remain fixed against the surrounding organ, for example the blood vessel, during the stress and strain to which the organ is subjected. The body should at the same time be elastically resilient radially and axially so as to have for example sufficient adaptability to follow pulsation of the blood or the bending of a limb. The body should also have sufficient inherent rigidity so as to maintain its shape at for example external pressure and must have sufficient strength to resist internal pressures.

In order to obtain these properties it is suitable to carefully select and adapt materials and dimensions on the thread elements of the body to the actual area of application. In addition to the obvious requirement that the material of the thread elements shall be compatible with the tissue, i.e. inter alia result in minimum reaction of rejection, non-toxic and enable cell growth, it may be generally the that the material should be rigid and elastic and not plastically deformable to any significant extent. The material may for example be monofilaments of polyesters, polyurethanes, polycarbonates, polysulphides, polypropylene, polyethylene, polysulphonates, stainless steel, and silver. In accordance with one aspect of the present invention, any of the implants/prostheses disclosed herein are formed at least partially and, more preferably, substantially completely of carbon fiber. The diameter of the monofilament should suitably lie in accordance with one aspect of the invention within the range of about 0.01 to about 0.5 mms, although other diameters may be used in modified embodiments.

In certain cases it is important that the angle alpha between the thread elements of the body, for example between 2 and 2a of FIG. 1A, when the body is expanded or is in an unloaded or nearly unloaded state is sufficiently large, inter alia to meet the above requirements. It has been found that the greater the angle alpha the higher the stability of the body under external pressure. The ideal from this point of view would be 180 degrees, which may not be practically possible. The angle as shown in FIG. 1A is about 160 degrees, which may in some instances be close to the upper limit.

Figure 10:
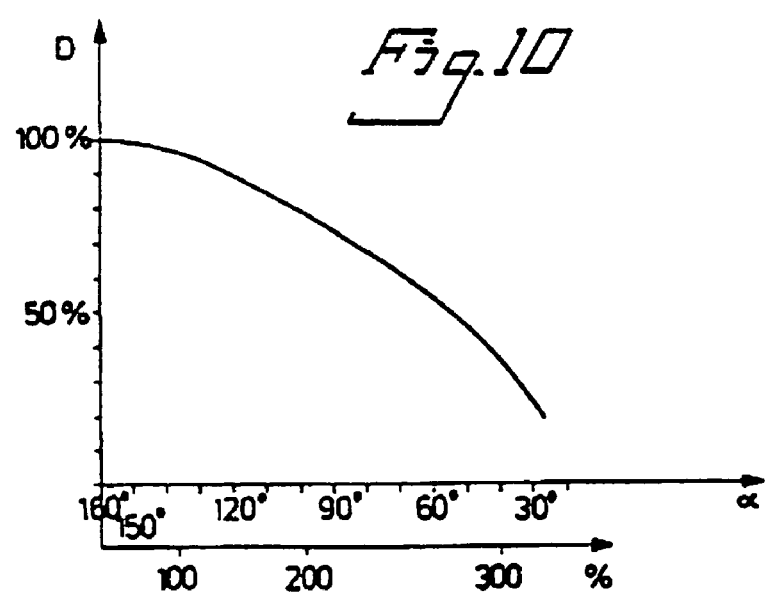
FIG. 10 shows a diagram of the diameter (D) of the body as a function of the angle alpha and of the elongation of the prosthesis in %.

In order to change the diameter of the body it is required, as indicated, that both ends of the body are axially displaced relative to each other. In FIG. 10 there is shown the general relation between this movement. The change in percent in diameter when the ends are moved away from each other has been plotted along the y-axis and along the x-axis the corresponding change in percent in length expressed as elongation. Along the x-axis there has also been plotted the angle alpha as a function of the diameter of the body.

As is shown from FIG. 10 the relative diameter reduction is small at the outset of the elongation process and the diameter has been reduced to the order of 90% when the elongation is 100%, referring to the starting position where the angle alpha is as close to 180 degrees as is practically possible. At an elongation of 200% the diameter reduction is 75% corresponding to an angle alpha of 100 degrees. The diameter reduction will then be accelerated at increasing elongation. Thus, an elongation increase from 250 to 300% results in a diameter reduction from 60% to 30%, i.e. a relatively large diameter change at a relatively small elongation. Within this range the angle is reduced from about 70 degrees to about 40 degrees. As indicated above it is in some cases desirable that the expanded body takes a position which is as far to the left on the curve of FIG. 10 as possible, i.e. the angle alpha should be as large as possible. Since the implanted body must engage against the vascular wall with certain pressure in order to remain fixed the diameter of implantation should be smaller than the diameter at free expansion.

When using expansible bodies according to the invention for implantation in blood vessels or other tubular organs the necessary expansion forces may be provided for example by elastic means, such as longitudinally extending elastic strings fixed at the crossing thread elements of helix configuration. By selecting a large angle alpha when the elastic means are fixed to the elements the requirements previously mentioned may be met in a simple manner.

The reason why a large value of the angle alpha is often desirable is the fact that the elastic properties of the prosthesis may be impaired with decreasing angle. Under for example exterior pressure in a radial direction the resistance to deformation is small and there is a risk for local axial displacement between the prosthesis and vascular wall, which can prevent cell growth at the site of displacement. Another reason for selecting a high value of the angle alpha is in those cases where a high expansion ratio is desired, i.e. a high ratio between diameter of the expanded body and the diameter thereof in contracted state. In order to obtain for example expansion ratio over 2 up to about 3 the angle alpha should exceed about 120 degrees. The selection of the angle alpha also varies depending on the material of the thread elements of the prosthesis. If a plastic material has been selected too small an angle alpha results in too high resiliency in the radial direction. In some other cases it may, however, be desirable to select a smaller angle alpha, namely in those cases where pronounced radial yield is desired.

Another case where a high value of the angle alpha might be desirable is applications wherein the prosthesis as applied will be subjected to a bending. One preferred application of the implants of the present invention is within vessels in connection with neurological applications. The resistance to flattening of the prosthesis will thus be higher the larger the angle alpha. Thus, it is suitable to select an angle alpha which is more than about 60 degrees, and an obtuse angle alpha could be particularly suitable. To provide for high resistance to external pressure or to enable high expansion ratios it is preferred to select an angle alpha of at least about 120 degrees.

From FIG. 10 it is clear that the body must be highly extended when using large angles alpha. To enable transluminal implantation through passages of small diameters the elongation starting from large angles alpha may be substantial and can be up to 300% and even more.

When implanting for example vessel prostheses or similar devices, to keep blood vessels open, it may be as a rule desirable to reach a pressure against the surrounding vascular wall which is at least about 100 mm Hg. There is also a highest pressure which should not be exceeded. This highest pressure varies from case to case but should not exceed for example about 500 to 1000 mm Hg when used as a vascular prosthesis. If the desired pressure will be provided by longitudinally extending elastic members or an elastic sleeve or membrane the necessary pressure for fixation can be obtained with reasonable forces when selecting a large angle alpha which is advantageous. Thus, calculations show that in smooth cylindrical engagement between vascular prosthesis and surrounding vascular wall there is required a total force of a few Newtons (.about.0.1–0.2 kp) to obtain fixation if the angle alpha is 150 degrees–170 degrees. This fact also contributes to the reduced risk of displacement of the implanted prosthesis under external pressure since the frictional forces arising are sufficient to prevent such displacement. If the angle alpha is for example 45 degrees there may be, however, required a force of about 10–20 Newtons (1–2 kp) which is practically disadvantageous.

In order that the prosthesis of the invention shall operate in a satisfactory manner, inter alia to give the necessary fixation when applied, such requirements should be met in regard to the elastic material resulting in the necessary expansive force. The material must also result in acceptable adherence to the thread elements of the body and should, of course, be biologically acceptable for implantation. The material shall thus have a low module of elasticity and should present a linear relation between force and elongation at least up to 250–600% elongation and should not possess significant hysteresis.

There is a group elastomers meeting the above requirements which has been found suitable for use in manufacturing expansible bodies according to the invention. Such elastomers are included within the group of materials called segmented polyurethanes (PUR), several of which are commercially available under trade names such as Pelethane (Upjohn), Biomer (Ethicon), Estane (BF Goodrich). These materials can be dissolved in suitable solvents to form solutions, from which thin elastic bands or thin-walled tubes can be prepared for attachment to the supporting thread elements of helix configuration forming the framework of the body.

When using a prosthesis in accordance with one aspect of the present invention as so-called grafts or vascular prostheses the wall of the prosthesis, as previously mentioned, can be porous, thin and compatible with tissue and be composed so as to enable growth of natural tissue, inter alia neointima. In addition to carbon fiber and resorbable plastics, segmented polyurethanes (PUR) are also suited for use to form such walls since the properties can be combined with the requirement of a wall having a very high elasticity. Such walls, regardless of the specific material or materials used, may be prepared in the form of a thin tube consisting of fibres of segmented PUR formed by extrusion from a solution of PUR. The fibres are attached to each other at the crossing points and the wall can be made with the desired porosity by suitable adjustment of for example fiber thickness and density. The resulting tube can surround the body or can be attached to the inside thereof. Alternatively, the thread elements of the body can be amalgamated with the tube material, suitably when preparing the tube.

In order to impart the desired expansional force to a vascular prosthesis bands of PUR, carbon fiber, resorbable plastic, and/or other materials may be combined with suitable porous wall material which can consist of monofilaments or multifilaments interwoven between the thread elements of the body or which can consist of a porous elastic wall prepared according to what has been described above.

It may be suitable to make the body or its bonds, sleeve or membrane from carbon fiber or a biologically degradable material, for example polylactide.

In another illustration of the present invention the type of stent to be deployed or retracted by an instrument according to the invention is a self-expanding braided stent, such as described above. However, it is to be understood that the instrument for deployment and/or retraction may be used for the placement of any expansible stent having a configuration and dimensions which enable it to be releasably held between the grip member and outer sleeve of the instrument. In accordance with on aspect of the present invention, the below-discussed stent comprises a resorbable or carbon fiber material.

In a preferred embodiment of the invention the core is hollow and this feature assists in the proper positioning of the instrument in a body canal. Thus it is possible to pass a guide wire into and along the body canal and pass the instrument over the guide wire until it is properly positioned in the body canal. In this embodiment the instrument includes an elongated, flexible, steerable guide wire located within and along the axis of the core. When the instrument is positioned in the body canal the guide wire may be retained within the instrument until the stent is deployed at the desired location and withdrawn together with the instrument or, alternatively the guide wire may be withdrawn prior to deployment of the stent so that correct positioning of the stent, while still within the instrument, may be verified, for example, by endoscopic or fluoroscopic means.

To facilitate movement of the core relative to the outer sleeve, the core can have a handle attached to its proximal end and the proximal end of the outer sleeve can terminate in a flange or handle.

It is to be understood that, as used herein, the term "proximal" means the end or part nearest to the operator of the instrument and the term "distal" means the end or part furthest from the operator. Thus the front end of the instrument which enters the body canal is the distal end. A significant feature of the instrument is the grip member and the significance of this feature is that it enables both deployment and retraction of the stent. In particular, the grip member is directly associated or integral with the core and is adapted to releasably hold a self-expanding stent within the outer sleeve. Thus, the grip member may be a sleeve or coating attached around the periphery of the core, an integral portion of the core or a length of the core having a larger outer diameter than the remainder of the core. Preferred embodiments include an instrument in which the grip member is a sleeve of material with a friction contact surface or a sleeve of material that will take a set, for example a silicone rubber or polyurethane. In each of these embodiments the sleeve material may have an outer surface which is substantially smooth and unbroken or an outer surface which is roughened or irregular. Alternatively, where the core itself is made from a material that will take a set the grip member may be an integral portion of the core. An advantage of this embodiment is that the grip member need not be a separate element which has to be attached or bonded to the core.

As used herein the term "friction" or "high friction" as applied to a material or its surface is intended to mean a material having a high coefficient of friction, i.e. a material whose surface offers high resistance to sliding motion; and the term "low friction" is intended to mean a material with a surface which offers little resistance to sliding motion and is relatively slippery.

Accordingly, since an important characteristic of the grip member is that it should be capable of gripping or holding a stent and this capability can be effective while the stent is retained within the instrument so that there is no slippage when the core is moved forward or backward relative to the outer sleeve, it is necessary when the grip member is a sleeve of material, that the material has a surface which offers high resistance to sliding motion. When the material is one which already has a high coefficient of friction the surface thereof which is in contact with the stent may be substantially smooth and unbroken. However, to increase the friction or enhance the inherent friction, the outer surface of the grip member may be roughened or irregular. In an alternative embodiment of the invention the gripping characteristic of the grip member may be achieved when the grip member comprises a coating of a releasable adhesive. In this embodiment the adhesiveness of the coating must be sufficient to retain or grip the stent without slipping while it is still within the instrument but weak enough to allow the stent to be released, by its own expansion, when it is free from the constraint of the outer sleeve. In a further embodiment of the invention the core itself is made from a high friction material, for example, a polyurethane, and the grip member comprises a length of the core, at or near the distal end of the core, having a larger outer diameter than the remainder of the core. In practice, the enlargement of diameter may be relatively small, of the order of about 0.01 inch, but it has been found that mounting the stent on this thicker portion of the core provides sufficient grip to enable the instrument to be operated as desired.

When the core itself is made from a material that will take a set, such a material being inherently of high friction, the larger diameter may not be necessary for the formation of the grip member. A "material that will take a set" is defined herein as a material that will be locally deformed in situ by the compression of the stent when it is pressed against the core by the outer sleeve and will retain the deformation so that the stent is effectively gripped thereby. In each of the above-described embodiments the grip member preferably is at least as long as the stent. When an expandable stent to be deployed by an instrument according to the invention is made from a plurality of cross threads, for example, plastic or metal filaments, and particularly metal filaments, such as by the braiding operation described above, the ends of the stent will have a number of exposed filament ends. To avoid snagging of these exposed ends, for example, into the wall of the outer sleeve, and to avoid consequential damage either to the outer sleeve or to the stent itself, it is advantageous to provide circumferential gaps adjacent the distal end and proximal end of the grip member to accommodate the respective ends of the stent. In this embodiment the ends of the stent tuck into the gaps thereby protecting them and preventing exposed filaments from snagging.

In contrast to the high friction characteristic of the grip member it is desirable that the inner wall of the outer sleeve has a low coefficient of friction to provide slidability and ease of movement of the stent-bearing grip member within the instrument. To achieve this characteristic it is preferable that the outer sleeve is a hollow catheter made from a low friction material, for example, a fluorocarbon polymer such as polytetrafluoroethylene. Furthermore, to avoid the snagging problem mentioned above, it may be advantageous to provide the inner surface of the outer sleeve with a layer of hardened material. Such material also should be a low friction material.

Additionally, when the outer sleeve is made from a relatively soft material, the soft distal end thereof may have a protective hard hollow cap, for example, made of metal, attached thereto. To facilitate proper placement of the instrument, it is advantageous to include one or more marker elements, each located at a predetermined position on the outer sleeve or core. In a preferred embodiment, each of the marker elements may be a band of metal or radiopaque material attached to the periphery of the outer sleeve, whereby correct placement of the instrument prior to deployment of the stent may be checked by fluoroscopy or any other imaging technique. The above features or any combination thereof may be included in the instrument to provide smooth operation, proper placement and avoidance of snagging or damage to the stent. In order to facilitate passage of the instrument into and along a body canal it also is advantageous to attach a flexible filiform to the distal end of the core. This embodiment also may avoid the use of a guide wire.

An embodiment of the invention illustrated in FIG. 12 comprises an outer sleeve 81 having an integral handle 82 at its proximal end. The distal end 83 of the outer sleeve is positioned within a body canal 84. Disposed axially within the outer sleeve is a hollow core 85 having a handle 86 at its proximal end. The distal end 87 of the core has a stepped up diameter where it meets the distal end of the outer sleeve so that it provides a smooth transition from the end of the outer sleeve, and is also within the body canal. A guide wire 88 passes axially through the hollow core. Attached around the periphery of the core at its distal end is a grip member 89 which releasably grips a self-expanding stent 90, shown here partly deployed at the proper location within the body canal. The stent may comprise materials and compositions as discussed above or below.

Figure 14:
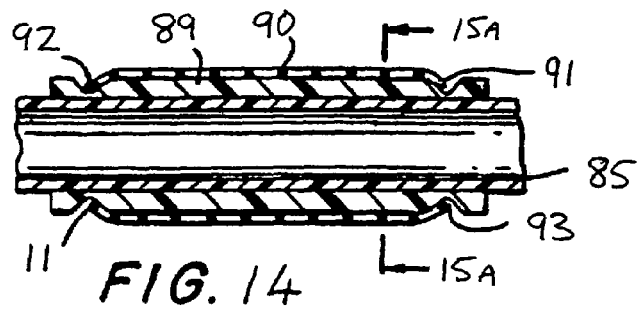
FIG. 14 is an enlarged cross section of one embodiment of a grip member.
Figure 15:
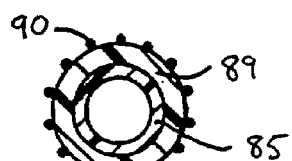
FIG. 15 is a cross-section through line 15A—15A on FIG. 14.
Figure 16:
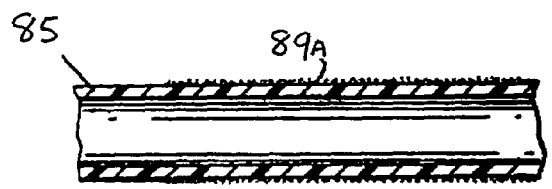
FIG. 16 and FIG. 17 are cross-sections of alternative grip members.

FIG. 13 is an enlarged side elevation showing a braided self-expanding stent 90, partly deployed from the distal end of the outer sleeve 91. This view shows the exposed ends of the wire filaments 91 which make up the stent. FIGS. 14 and 15 illustrate a grip member 89 made from a high friction material attached around the periphery of a hollow core 85. The grip member has circumferential gaps 92, 93 adjacent its distal end and proximal end, respectively, which accommodate the ends 91 of the stent, thereby avoiding snagging into the inner wall of the outer sleeve. FIG. 16 illustrates a grip member 89A which comprises a coating of releasable adhesive around the periphery of the inner core 85.

Figure 17:
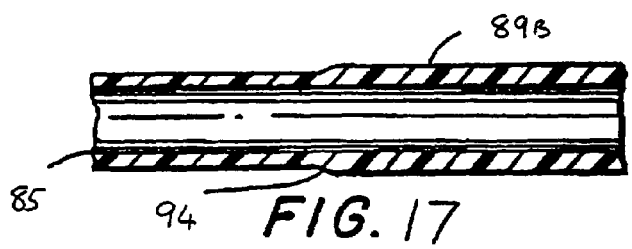
Figure 18:
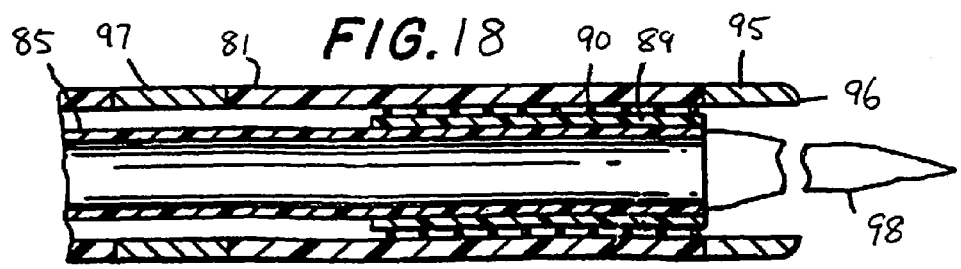
FIG. 18 is a side elevation of part of an instrument according to the invention showing other features.
Figure 19:
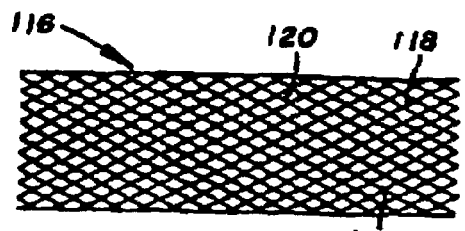
FIG. 19 is a side elevation of a self-expanding stent constructed according to the present invention.
Figure 20:
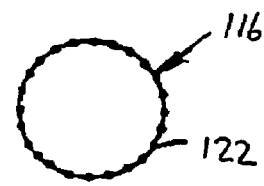
FIG. 20 is an end elevational view of the stent.

FIG. 17 illustrates, in cross-section, an embodiment in which the hollow core 85, is made from a high friction material, for example, a polyurethane, and the grip member 89B comprises a length of the core having a larger diameter than the remainder of the core, indicated schematically by the step 94. If the high friction material is a material that will take a set the grip member may be simply a portion of the core without the enlargement of diameter. FIG. 18 is a side elevation, partly in section, of part of an embodiment showing additional features. In this embodiment the outer sleeve 81, preferably made from polytetrafluoroethylene, has a smooth metal rim 95 at its distal end to prevent snagging from the ends of the stent 90. Preferably the distal end 96 of the metal rim is rounded to facilitate passage along the body canal. Additionally, the metal cap may serve as a marker element for fluoroscopic monitoring of the placement of the instrument within the body canal. Additional or alternative marker elements 97 may be provided at predetermined positions on the outer sleeve and/or on the core (not shown). Alternatively the metal cap and or marker elements 97 may be composed of carbon fiber, to permit for example fluoroscopy or any other imaging technique. A flexible filiform 98 may be attached to the distal end of the core 85 to facilitate passage of the instrument along a body canal in a known manner. Deployment of a stent within a body canal in accordance with the method of the invention may be performed by using any of the embodiments illustrated in the drawings and described above.

A self-expanding stent is introduced into the instrument in a manner known in the art and pre-located on the grip member. The grip member bearing the stent is withdrawn into the instrument so that the whole of the stent is within the outer sleeve, close to the distal end thereof, and is constrained by the outer sleeve. The instrument containing the stent is then introduced into the body canal, with or without the aid of a guide wire, and passed into the canal until it reaches a position for proper placement of the stent. The introduction and passage of the instrument in the body canal may be facilitated when a filiform is attached to the distal end of the core as described hereinabove. The positioning of the instrument within the body canal may be monitored and verified by any means known in the art, for example, by use of an endoscope, or by fluoroscopy or any other imaging technique. To assist fluoroscopic examination, the stent comprises carbon fiber, or in the alternative the outer sleeve or core of the stent may be comprised of carbon fiber, or one or more marker elements may be located at a predetermined position on the outer sleeve or core as described hereinabove.

When the correct position for proper placement of the stent is reached and verified, the stent is then deployed by moving the outer sleeve relative to the core. This operation is performed by holding the handle at the proximal end of the core so that the core, together with the grip member holding the stent, remains stationary, gripping the handle at the proximal end of the outer sleeve and withdrawing the latter towards the core handle so that the outer sleeve moves backward, thus exposing the stent, which, free from the constraint of the outer sleeve, expands to its expanded state. Before the stent is completely deployed from the instrument, the positioning thereof in the body canal is checked. If the position is correct then the withdrawal of the outer sleeve is continued until the stent is clear of the instrument and the instrument is then withdrawn from the body canal. However, if the monitoring reveals that the stent is not in its proper position then it may be retracted back within the outer sleeve simply by moving the core backwardly relative to outer sleeve using the handles on the core and outer sleeve. The instrument, containing the retracted stent, then may be re-positioned as required and the deployment operation repeated with the stent in its correct position.

Deployment of the stent by withdrawing the outer sleeve relative to the core has the advantage that it avoids the problem of the distal end of the stent digging into or snagging against the wall of the body canal, which problem might occur if the stent were to be pushed into the body canal from behind. The capability of being able to retract the stent so that the instrument may be repositioned without damage to the stent or injury to the body canal is a distinct advantage of the present invention. Further, it is important that the stent be easily imaged during the follow-up of the patients, in order to determine the stability of the location of the stent. Carbon fiber can be a suitable material from which to create the core. Additionally, it will provide the necessary visibility in imaging so as to facilitate patient follow-ups.

Another alternative form embodiment of the self-expanding prostheses (e.g., stent) that can be made from carbon fiber comprises a flexible tubular body that is composed of several individual rigid but flexible thread elements having spring properties. Each thread element extends in coil configuration with the center line of the body as a common axis, a number of elements having the same direction of winding but axially displaced relative to each other crossing a number of elements also axially displaced to each other but having the opposite direction of winding. These elements suitably form a braided configuration which by means of suitable members can be implanted in a radially contracted condition in for example blood vessels, urinary tracts, bilious tracts, gorges, or other positions that are difficult to access so that it after self-expansion will be fixed at the implantation site thus providing permanent support for the surrounding walls of the vessel.

The crossing thread elements are preferably symmetrically arranged in the form of a braid. If the known prosthesis shall be used for example for widening a narrow section in a blood vessel the flexible tubular body is suitably inserted arranged in a radially contracted state at the tip of a flexible instrument, for example percutaneously in a blood vessel. The device is then transluminally transferred to the relevant narrow section of the blood vessel, and the tubular body is then allowed to expand and in a radially expanded state it is released from the instrument so that it remains at the implantation site under self-fixation and the instrument can be removed. In this connection the diameter of the body in an unloaded and expanded state should be chosen somewhat larger than the inner diameter of the vessel. This results in a certain permanent pressure or engagement against the inner wall of the vessel which pressure has to be sufficiently large to keep the previous restriction open at the same time as an effective self-fixation will be obtained.

The thread elements are preferably built up as monofilaments, i.e. they consist of single thread elements (e.g., carbon fiber or resorbable plastic). Monofilaments have the advantage of being smooth on their external surface such that they can glide smoothly past each other.

A prosthesis of the type described above is suitably manufactured starting from a tubular braid manufactured in a braiding machine known per se wherein usually a number of bobbins, each one containing its thread element, are movably arranged in a ring about a center, so that each bobbin can rotate about its own axis in connection with dewinding the respective thread elements, at the same time as the bobbins are moved about in a zig-zag-shaped circular movement about this center. A number of bobbins are arranged in the same manner in a ring but are moved in a zig-zag-shaped circular movement in the opposite direction in relation to the first-mentioned group of bobbins. The braid is suitably deposited around a tubular axis in the center of the machine, and the thread elements can form different braiding patterns, i.a. depending on how the bobbins are brought to rotate. Tubular prosthesis of a suitable length can then be severed from the manufactured tubular braid.

In practice it has been found that in the practical use of prosthesis of the type described above it is necessary for several reasons that the thread elements forming the tubular body have a dimension which is as small as possible but which at the same time provides for the necessary force against the wall of the vessel so that the tubular body obtains a small wall thickness so as not to accommodate too much space when for example implanted in fine blood vessels so that a too large reduction of the flow area for the blood will result. This is particularly important with prostheses of a relatively small diameter, for example for use for implantation into the coronary vessels of the heart. Moreover, a small dimension of the thread elements is essential in those cases where one wishes to obtain a high expansion capacity of the prosthesis, i.e. a high ratio between the prosthesis in an expanded state in relation to the prosthesis in a radially contracted state. Another reason as to why small dimensions of the thread elements are desirable is the fact that the prosthesis in a contracted state shall be accommodable in an implantation device of small diameter, for example for percutaneous implantation. Finally, small thickness of the thread elements is an important advantage from a biological point of view, since the prosthesis built up from fine thread elements in an implanted state substantially facilitates coverage of the prosthesis with a layer of natural cells which in a blood vessel prevents the risk for thrombosis. For this reason it has been found that the thread elements must be made of a flexible, rigid, resilient material, for example a spring steel, a spring alloy or the like, the rigidity of the material in combination with its spring properties being of an essential importance. However, it has been found that it is in practice coupled with great difficulties to make a self-expanding prosthesis starting from a material of such properties.

Provided is an elastic, self-expanding prosthesis, the supporting construction of which includes a flexible tubular body which is composed of a plurality of individual rigid but elastically flexible thread elements having spring properties. The tubular body is designed such that the remaining tension of the thread elements in the state in which they constitute supporting elements in the tubular body, at least at the end sections of the body are adjusted so that diameter of an unloaded helix-shaped thread element, at least at its end sections, when removed from the other elements forming the tubular body is not more that about 60% larger than the diameter of the body in an unloaded condition. By the diameter of the thread element there is meant in the present context the diameter of the cylinder within which the helix-shaped thread element can be considered to be inscribed.

In one embodiment at least one of the thread elements at each crossing site is deformed in such a manner that it at least partly encloses the other thread element. When using thread elements of circular cross section the expression "at least partly circumscribes" but instead of point contact between crossing thread elements line contact would be obtained. The deformation of the outer thread element at each crossing site can be constituted by a breaking over the inner thread element at the area of contact between the two elements. This means in other words that each thread element of the tubular body extends alternatingly radially inside and radially outside the crossing thread elements at the respective crossing points, the number of thread elements in one rotational direction being the same as the number of thread elements in the other rotational direction. In the following this configuration will be called "one above/one below".

The deformation of at least the outer thread element at each crossing site as described in the above embodiment results in the important advantage that relative sliding movement between the thread elements will be prevented or at any rate made quite difficult, and this in turn means that the solution of the above-indicated problem of the outward bending of the thread ends will be further facilitated. Alternative deformation techniques are conceivable, and another example is one where both thread elements at each crossing site are deformed in the opposite direction relative to each other. The deformation may also be constituted by flattening of the juxtaposed surfaces of crossing thread elements at the crossing site. It has also been surprisingly found that by using the above-mentioned deformation there is also gained the advantage that the disturbing tension of the thread elements is reduced so that if a thread element is removed from the prosthesis it has a helix shape of largely the same pitch as when it was part of the prosthesis, i.e. by the deformation one can also remove a great part of the tensions.

The thread elements may all comprise carbon fiber or alternatively only some of the threads may comprise carbon fiber to provide more or less rigidity, and to allow for various mechanical aspects and/or clearer imaging of the stent.

According to another aspect of the invention it has been found that in certain cases, particularly in prostheses of small diameter and built up of fine thread elements, it is preferred to design the body so that at its ends in an unloaded condition it widens conically outwardly to a diameter which is greater than the diameter of the rest of the body. The conical widening outwardly can suitably be to a diameter which is at most about 20% greater than the diameter of the body in the intermediate section. The reason why this conical widening of the end sections of the prosthesis results in substantial advantages is the fact that in practice it has been found that the ends of the prosthesis at radial compression of same are subjected to a greater reduction of the diameter than the rest of the body. Since the prosthesis is intended to be implanted in a vessel of somewhat smaller diameter than the prosthesis has in an unloaded state the prosthesis when implanted will therefore obtain a substantially constant diameter across its full length. The desired conicity at the ends can suitably be obtained by adjusting the remaining tension of the thread elements or a selected deformation at the crossing sites.

In order to obtain a prosthesis with filtering function it may optionally be suitable to design at least one end of the body with a diminishing diameter, whereby it can serve as a filter when applied. According to yet another aspect of the invention the prosthesis can comprise extra threads of other materials in order that the prosthesis shall obtain the desired porosity. It may in this case also function as a graft.

One embodiment of such prosthesis according to the invention resides in the feature that in connection with the braiding operation in a conventional braiding machine known per se the tubular body is braided under application of such tension to each individual thread element that they are permanently deformed and bent over the under-lying thread element at the crossing point. By applying this technique there will be obtained better adaptation of the remaining tension of the thread elements and also better fixation by bending of the crossing thread elements in relation to each other while maintaining flexibility of the prosthesis.

An alternative process according to the invention to provide for deformation of the thread elements in connection with the crossing points is to subject the body after its manufacture to mechanical deformation, so that at least one of the thread elements at each crossing point at least partly circumscribes the other thread element, so that sliding movement between the crossing threads is prevented, whereas rotational movement under low friction between the thread elements at the crossing points will be made possible. Such mechanical deformation can be provided for example by hammering, mechanical or isostatic pressing or blastring. The mechanical deformation obviously mainly results in deformation of the outer thread element at each crossing point so that it at least partially will circumscribe the underlying thread element.

Another configuration would be the construction of a stent made of serially arranged segments of the design as outlined above, with the exception that each individual segment is linked by a less rigidly constructed weave, which will permit sufficient bending to enable the stent to negotiate a tortuous structure. The linkage weave linking each segment could be an extension or component of the individual segments.

As previously indicated it may be desirable in certain embodiments to use as material for the thread elements materials, which are medicinally acceptable, are rigid and have adequate or extreme spring properties. Since it may be desirable that the wall of the prosthesis be as thin as possible and exert a certain sufficient pressure against the wall of the vessel at the same time as the prosthesis shall have a high expansion number, it may be preferred in accordance with these certain embodiments that the thread material should have such high "springiness" or energy storage capacity as possible in view of the other design parameters.

A carbon fiber prosthesis or stent may be positioned by means of compression and simultaneous axial extension over the tip of a small flexible implantation instrument provided with a central channel to enable i.e. insertion of a so called guide wire in the channel to facilitate insertion of the prosthesis. The prosthesis is placed in a compressed state, surrounded by a thin plastic tube belonging to the tip of the instrument.

In another embodiment, illustrated in FIGS. 19–26, the carbon fiber stent comprises an open mesh or weave construction, consisting of two sets of oppositely directed, parallel and spaced apart helically wound strands or filaments indicated at 118 and 120, respectively. The stent comprises an elongate cylindrical core substantially uniform in lateral cross-section and having a core diameter, and an elongate tubular case or shell substantially uniform in lateral cross-section and having a case inside diameter, wherein one or both of the core and case is formed of a carbon fiber. In another embodiment, one of the core and case is formed of a carbon fiber and the other is formed of a resilient material having a yield strength (0.2% offset) of at least 150,000 psi, wherein the core diameter is less than the interior diameter of the case, and the lateral cross-sectional area of the core and case is at most ten times the lateral cross-sectional area of the core; the core is inserted into the case to form an elongate composite filament in which the case surrounds the core.

The sets of strands are interwoven in an over and under braided configuration so as to form multiple intersections, one of which is indicated at 122. The self-expanding stent 116 is illustrated in its relaxed state, where no external stress is applied. The filaments or strands of the stent 116 are resilient, permitting a radial compression of the stent into a reduced-radius, extended-length configuration suitable for transluminal delivery of the stent to the intended placement site. By selectively controlling the angle between the oppositely directed helical strands the degree of axial elongation for a given radial compression may be predetermined.

Further, it is advantageous in accordance with one aspect of the invention to form a prosthesis with substantial open space to promote embedding of the stent into tissue, and fibrotic growth through the stent wall to enhance long-term fixation. A more open construction also enables substantial radial compression of the prosthesis for deployment. In a typical construction suitable for transluminal implantation, the filaments can have a diameter of about 0.1 millimeter (0.004 inches), with adjacent parallel filaments spaced apart from one another by about 1–2 millimeters (0.04–0.08 inches) when the stent is in the relaxed state.

Figure 21:
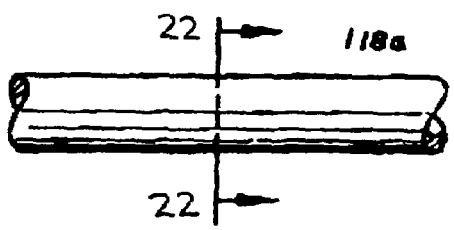
FIG. 21 is an enlarged partial view of one of the composite filaments forming the stent.
Figure 22:
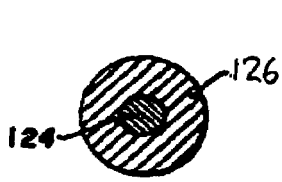
FIG. 22 is an enlarged sectional view taken along the line 4—4 in FIG. 3.
Figure 23:
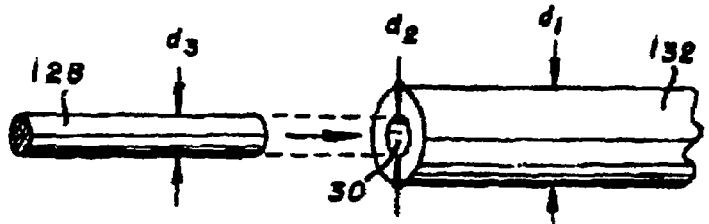

Fluoroscopic imaging of a conventional open weave prosthesis may be difficult. Due to their diameters and/or the materials involved, the filaments may exhibit a relatively poor contrast to body tissue for fluoroscopic imaging purposes. The filaments may also require a high degree of spatial resolution in the imaging equipment involved. Thus, a stent recognizable on X-ray film may not be distinguishable for real time imaging, due to the relatively poor spatial resolution of the video monitor as compared to X-ray film. According to the present invention, however, prosthesis 116 is substantially more amenable to fluoroscopic imaging, due to the construction of strands 118 and 120 and the use at least in part of carbon fiber as construction material either in those strands alone or multiple strands. In particular, the strands cooperate to present a sufficiently radiopaque mass at the tangents of device 116 (parallel to the X-rays) for satisfactory real time imaging. As seen in FIGS. 21 and 22, a filament 118a of the prosthesis is of composite construction, with a radiopaque core 124 comprises carbon fiber surrounded by and concentric with an annular resilient case 126.

The process can begin with insertion of a solid cylinder or wire 128 of the core material into a central opening 130 of a tube 132 of the case material. Core wire 128 and tubing 132 are substantially uniform in transverse or lateral sections, i.e. sections taken perpendicular to the longitudinal or axial dimension. In general, the wire outer diameter is sufficiently close to the tubing inner diameter to insure that core or wire 128, upon being inserted into opening 130, is substantially radially centered within the tubing. At the same time, the interior tubing diameter must exceed the core outside diameter sufficiently to facilitate insertion of the wire into an extended length of wire and tubing, e.g. at least twenty feet.

Figure 24:
Figure 25:
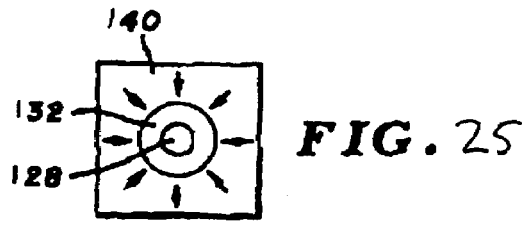

Insertion of the core into the tube forms a composite filament 134. More particularly, in the illustrated example composite filament 134 is drawn through three dies, indicated at 136, 138, and 140, respectively, as seen in FIG. 24. In each of the dies, composite filament 134 is cold-worked in radial compression, causing the case tube 132 and the tantalum core wire 128 to cold flow in a manner that elongates the filament while reducing its diameter. Initially, case tube 132 is elongated and radially reduced to a greater extent than core wire 128, due to the minute radial gap that allowed the insertion of the core into the tube. However, the radial gap is closed rapidly as the filament is drawn through die 136, with subsequent pressure within die 136 and the remaining dies cold-working both the core and case together as if they were a single, solid filament. In fact, upon closure of the radial gap, the cold-working within all dies forms a pressure weld along the entire interface of the core and case, to form a bond between the core and case material.

As composite filament 134 is drawn through each die, the cold-working induces strain hardening and other stresses within the filament. Accordingly, one or more heating stages are provided, e.g. furnace 142. At each annealing stage, substantially all of the induced stresses are removed from the case and core, to permit further cold-working. Each annealing step is accomplished in a brief time, e.g. in as few as one to fifteen seconds at annealing temperature, depending on the size of composite filament 134. While FIG. 24 illustrates one cold-working stage and annealing stage, it is to be understood that the appropriate number of stages is selected in accordance with the desired final filament size, the desired, degree of cross-sectional area reduction during the final cold-working stage, and the initial filament size prior to cold-working. In an alternative embodiment the carbon fiber material may instead comprise a mixture of carbon fiber and other metals that have the capability of being cold-worked.

In FIG. 26, several filaments or strands 134*a*–*e* are helically wound about a cylindrical form 148 and held in place at their opposite ends by sets of bobbins 150*a*–*e* and 152*a*–*e*. Strands 134*a*–*e* can be individually processed, or individual segments of a single annealed and cold-worked composite filament, cut after the final cold-working stage. In either event, the filaments cooperate to form one of the two oppositely directed sets of spaced apart and parallel filaments that form a device such as stent 116. While only one set of filaments is shown, it is to be understood that a corresponding group of filaments, helically wound and intertwined about form 148 in the opposite direction, are supported by corresponding bobbins at the opposite filament ends.

FIG. 27 illustrates two filaments 134*a* and 154*a*, one from each of the oppositely wound filament sets, supported by respective bobbins 150*a*/152*a* and 156*a*/158*a*. The filaments overlay one another to form several intersections, one of which is indicated at 162. When the filaments are properly tensioned, a slight impression is formed in the overlying filament at each intersection. These impressions, or saddles, tend to positionally lock the filaments relative to one another at the intersections, maintaining the prosthesis configuration without the need for welding or other bonding of filaments at their intersections.

FIGS. 30 and 31 show a further alternative composite filament 180, consisting of a central radiopaque core 182 comprised of for example carbon fiber, an outer annular structural case 184, and an intermediate annular layer 186 between the core and the case. Intermediate layer 186 provides a barrier between the core and case, and is particularly useful in composite filaments employing core and case materials that would be incompatible if contiguous, e.g. due to a tendency to form intermetallics. Materials suitable for barrier layer 186 include tantalum, niobium and platinum, and in other embodiments may comprise carbon fiber. As suggested by FIG. 30, the core, barrier layer and case can be provided as a cylinder and two tubes, inserted into one another for manufacture of the composite filament as explained above.

FIG. 32 illustrates another alternative embodiment composite filament 188 having a central radiopaque core 190, (comprised of for example carbon fiber or carbon fiber mixed with easily cold-welded metal), a structural case 192, and a relatively thin annular outer cover layer 194. Composite filament 188 is particularly useful when the selected mechanical structure lacks satisfactory biocompatibility, hemocompatibility, or both. Suitable materials for cover layer 194 include tantalum, platinum, iridium, niobium, titanium, carbon fiber and stainless steel. The composite filament can be manufactured as explained above, beginning with insertion of the radiopaque core of for example carbon fiber into the structural case, and in turn, inserting the case into a tube formed of the cover material. Alternatively, cover layer 194 can be applied by a vacuum deposition process, as a thin layer (e.g. from ten to a few hundred microns) is all that is required.

The above described composite filaments can combine the desired structural stability and resiliency, with radio-opacity that can allow in vivo imaging of the device composed of the filaments, during deployment and after device fixation.

Resilient or self-expanding prostheses can in accordance with one aspect of the invention be deployed without dilation balloons or other stent expanding means. Self-expanding stents can be preselected according to the diameter of the blood vessel or other intended fixation site. Further, the self-expanding stent remains at least slightly elastically compressed after fixation, and thus has a restoring force which facilitates acute fixation.

Figure 33:
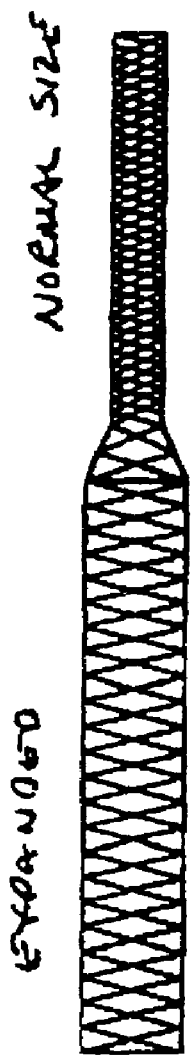
FIG. 33 illustrate a stent or prosthesis in accordance with one embodiment of the present invention.

FIG. 33 illustrate a stent or prosthesis in accordance with one embodiment. The intravascular device of the present invention can be deployed to the site of vascular pathology and possess the following properties in connection with the treatment of vascular narrowing or out pouching. These properties include (1) the ability to be selectively expandable to occlude a narrow vascular segment, or to occlude the opening of an out pouch, (2) the ability to re-establish vessel wall anatomy, and (3) the construction with material which would permit radiographic detection without distortion of the surrounding anatomic relations. An intravascular stent composed of MR compatible material such as carbon fiber or lactic acid polymers designed to possess memory of selective shapes and sizes, or which can be molded intravascularly to conform to the intenal anatomy of the vessel, either to expand a narrow segment or to occlude the opening of an out pouch, is herein disclosed.

Stents in the category of possessing memory of selective shapes and sizes must be made of materials which are compatible with scanning techniques which permit the visualization of anatomical structures in the surrounding of the stent such that its relationship with the surrounding can be defined with the least distortion. One such material would be carbon fiber. Conceivably, other materials with similar properties can also be used with any of the carbon fiber structures disclosed herein, such as any of the materials described in U.S. Provisional Application No. 60/237,784 filed Oct. 4, 2000, the contents of which are incorporated herein by reference.

Such materials may take the form of a sheet or be composed of thin threads woven in such a manner, which will permit the stents to assume the desired form and size (i.e., with predetermined memory) upon deployment. Desirable features of the stents would be the ability of the stents to negotiate through multiple bends in the vascular tree without loss of the ability to manipulate them. This has been the major deficiency in current stent designs rendering them too stiff, and thus, usable primarily in situations where the vessels are relatively straight such as the cervial carotid arteries, the vertebral/basilar arteries or the coronary arteries.

The designs which would likely permit this, in addition or supplemental to those discussed above, include ones in which elements of the stents can be manipulated to move relative to each other. An example would be a sliding weave pattern in the thin threads which are so woven that the part of the stent on the inside of a bend would be bunched closer together while the part on the outside of the bend would stretch out. Another design would be a construction of the stent, which incorporates multiple cylindrical elements linked together in series such that parts of each cylindrical element could be manipulated to be closer (to accommodate the inside of a bend) or farther apart (to accommodate the outside of a bend). In this configuration, the intervening portions of the stent linking the cylindrical elements together would form a smooth surface not to create any turbulent blood flow which in turn would lead to clot formation and occlusion of the vessel.

Such stents can be deployed using currently available deployment mechanisms such as, in addition or supplemental to those discussed above, the ensheathment in a catheter, which is brought to the site of deployment. Upon correct positioning of the stent, it is pushed out to the vascular lumen where it expands in a preformed manner to distend the vessel and/or to occlude any out pouching. Another method of deployment would be the delivery of the stent to the site on the external aspect of a balloon of a balloon catheter. Upon correct positioning of the balloon, it is then inflated to the desired size thus forcing the stent onto or against the vascular wall. The stent is then detached in situ. Since it is so constructed with memory to assume a preformed shape and size, it will maintain the vessel open in the desired configuration.

Stents which can be molded intravascularly to conform to the internal anatomy of the vessel in accordance with an aspect of the invention are composed of materials, which can be molded to a desired shape and size inside a vessel to conform to its anatomy. The material must also be flexible enough to allow the stent to be manipulated through bends in the vascular tree. One such material would be the amino acid polymers which can be formed to assume a certain shape and size, and which upon heating, can be molded into any form or size within defined constrains.

Stents of this type can be delivered to the vascular site on the external surface of a balloon catheter. In this stent design, the stent is configured to assume the shape of a cylinder of different length or a sequence of spirals so that it can be secured onto the external surface of the catheter/balloon, which will then deliver it to the intended vascular site. These stents should be composed of material to allow them to be expanded reversibly to form a cylinder of larger diameter either through its inherent design (e.g., a series of spirals) or under specific conditions such as heating to a defined temperature. Once the stent is in the expanded state, and maintained in this state by the inflated balloon, it can be maintained in this expanded state by itself because of its inherent design or through termination of the expanding condition (e.g., termination of heating). The moment it is deemed that the stent is correctly deployed (i.e., to be in the correct position and in the correct shape and size), it can be detached from the balloon by deflating the balloon. The deflated balloon can then be removed from the vessel with the catheter. There should also be memory in the initial configuration of the stent such that should the deployment of the stent and its expanded shape and size not be ideal, removal of the configuration condition such as the termination of heating would allow it to shrink back to its original smaller size and shape. In so doing, it can be resecured onto the external surface of the catheter and/or balloon to be redeployed.

The deployment balloon catheter is composed of a catheter at the tip of which is an inflatable balloon of defined length and expandable diameter. Impregnated in the catheter as well as the balloon surface are heating elements. These heating elements in the balloon wall can be so configured to be expandable as the balloon is inflated and yet be able to deliver a consistent and uniform degree of heating throughout the surface of the balloon, which is in contact with the stent. There may also be elements on the external surface of the catheter and/or balloon, which will secure the stent onto its surface such that the stent will not be detachable until it is positioned in the desired location inside the blood vessel.

Stents of this design are delivered to the vascular site on the external surface of the balloon. It is maintained in a flexible state on account of its construction (e.g., a series of spirals) or under constant heating through the heating elements on the surface of the balloon so that it can negotiate the bends of the vascular tree. Upon arrival at the desired vascular site, the balloon is inflated to expand the stent to the desired size and shape. The stent can be expanded because of its inherent design (e.g., a series of spirals), or through heating with the heating elements in the wall of the balloon.

In the situation of a narrowed artery, inflation of the balloon is used not only to expand the stent but also to dilate the vessel in turn. In the situation of the arterial out pouching, the stent will be expanded to conform to the internal configuration of the blood vessel but in such a position to occlude the opening of the out pouching. Once the stent is in place on the inner surface of the blood vessel, either its specific design (e.g., a series of spirals) would maintain it in place in the expanded state, or it is maintained in the expanded state by termination of the condition, which allows it to be expanded. In the latter situation, heating allows the balloon to expand the stent to the desired shape and size. Cessation of heating would allow the stent to maintain its expanded shape and size on the inner surface of the vessel wall. After it is determined that the stent is correctly deployed, the balloon is then deflated and removed from the circulation. The stent is left at the vascular site either to maintain the vessel in its more dilated state or to close the opening of the out pouching on the side of the vessel.

Should the initial deployment not be ideal and that the stent needs to be repositioned, the design (e.g., a series of spirals) which permits it to be maintained in the expanded state should also permit it to be reversibly returned to the non-expanded state so that it can be retrieved and secured onto the surface of the balloon to be redeployed. If the design is such that the stent is composed of material to allow it to be expanded reversibly to form a cylinder of larger diameter under specific conditions such as heating to a defined temperature, the stent material should possess such memory such that the stent can be returned to its origin shape and size by removal of the configuration condition such as the termination of heating and deflation of the balloon. This would allow it to shrink back to its original smaller size and shape. In so doing, it can be resecured onto the external surface of the catheter and/or balloon to be redeployed.

FIGS. 34–37 illustrate a resorbable stent or prosthesis ("resorbable prosthesis") in accordance with one aspect of the present invention. In accordance with one aspect of the invention, the stent or prosthesis comprises any non-metallic (e.g., polymer or plastic) material. In the illustrated embodiment, the stent or prosthesis comprises a resorbable material. The resorbable prosthesis can be either injection molded or machined to have an original shape (i.e., a natural shape that the material has before being heated to its glass transition temperature and deformed). The original shape preferably approximates the outer surface of the balloon, so that the resorbable prosthesis can be closely formed around the outer surface of the balloon. Alternatively, the resorbable prosthesis may be formed to have an original shape which is different than that of the outer surface of the balloon, and the resorbable prosthesis may be heated to its glass transition temperature and formed relatively closely around the balloon. For example, the resorbable prosthesis may be formed to have a cylindrical shape and a diameter less than the maximum diameter of the balloon, and, subsequently, the resorbable prosthesis can be placed around the balloon. The resorbable prosthesis is then brought to its glass transition temperature and formed around the balloon as the balloon slightly stretches (i.e., increases the diameter of) the resorbable prosthesis at glass transition temperature. The resorbable prosthesis is then cooled with the balloon remaining in the same shape so that the resorbable prosthesis fits snugly around the balloon, thus yielding the configuration of FIG. 34.

The balloon catheter preferably comprises conductors for transferring energy to the resorbable prosthesis to thereby bring the resorbable prosthesis to its glass transition temperature. The conductors are preferably distributed on the surface of the balloon to transfer thermal energy to the resorbable prosthesis. A control may be provided for selectively regulating the electrical energy used to heat the resorbable prosthesis. The expandable balloon, may contain an inner wall lined with conductors which can be heated. The balloon may also be heated using a fluid that can be heated to the glass transition temperature of the resorbable prosthesis.

Figure 34:
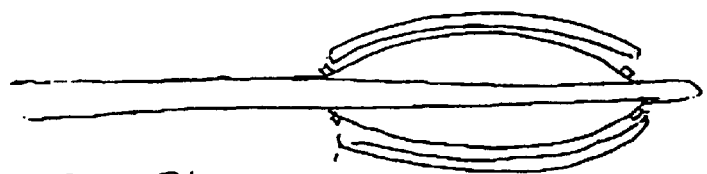
FIG. 34 depicts a balloon catheter with a stent attached in its contracted position.

FIG. 34 illustrates the resorbable prosthesis in a position coupled to a balloon. The balloon may comprise optional protrusions at the proximal and distal ends of the balloon in the form of discrete protrusions or proximal and distal rings. Additionally or alternatively, the resorbable prosthesis can be weaved in a manner in which the inside is relatively rough to create a frictional contact between the resorbable prosthesis and the balloon when the two are coupled together. Moreover, other attachment means which are known in the art may be used to secure the resorbable prosthesis.

Figure 35:
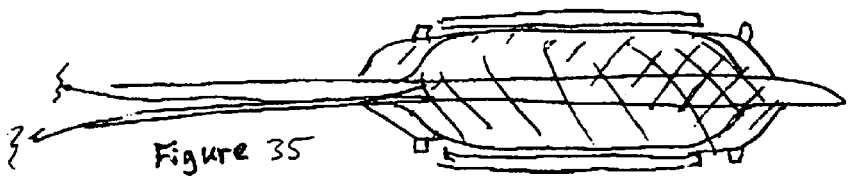
FIG. 35 shows the balloon catheter in an expanding state, while heat is applied through the heating source, and the corresponding expansion of the stent.
Figure 36:
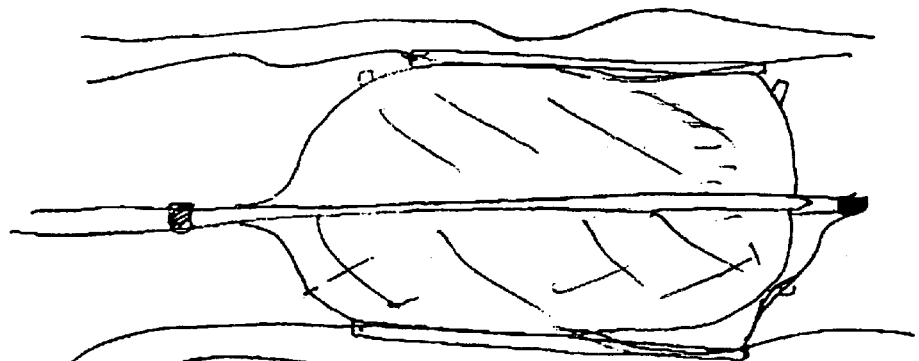
FIG. 36 depicts the fully expanded balloon catheter and the maximally expanded stent.

In FIG. 35 the resorbable prosthesis is first heated by the balloon to its glass transition temperature. Subsequently, the balloon is expanded to thereby expand the resorbable prosthesis as shown in FIGS. 35 and 36. Any conventional means of expanding the balloon may be used. As presently embodied, fluid is passed through the center of the balloon, expanding the heated balloon. The fluid may comprise, for example, a saline solution or air. The resorbable prosthesis, which is heated to its glass transition state, correspondingly increases in diameter as the balloon expands. The balloon is preferably configured to expand the resorbable prosthesis into a cylindrical shape to match the inner wall of the vessel. In other embodiments, the balloon can be configured to form the resorbable prosthesis into other shapes.

The balloon's surfaces will press against the resorbable prosthesis, reforming the resorbable prosthesis so that it is no longer concave similar to the resorbable prosthesis in FIG. 35. Thus, once the temperature decreases and the balloon begins to deflate the now cylindrically-shaped resorbable prosthesis will no longer be affixed to the balloon, and will remain in its expanded configuration, allowing for removal of the balloon catheter.

FIG. 36 portrays the resorbable prosthesis at its maximally expanded state, at which time energy is no longer transferred to the resorbable prosthesis so that the resorbable prosthesis may cool below its glass transition temperature to body temperature, with surrounding liquids in the vessel rapidly absorbing much of the energy from the resorbable prosthesis as the resorbable prosthesis cools.

Figure 37:
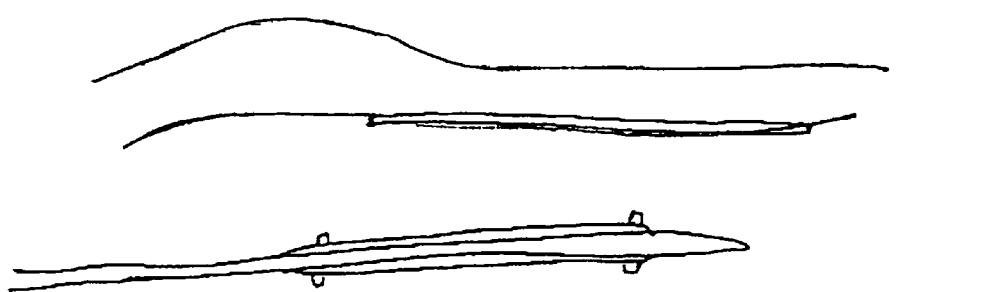
FIG. 37 depicts the deflated balloon catheter as it is being withdrawn from the body cavity, with the stent remaining in place.

The balloon is then deflated and removed from within the resorbable prosthesis as portrayed in FIG. 37. The resorbable prosthesis will hold this shape until its temperature is once again raised to the glass transition temperature.

The balloon, in one embodiment, can be re-inserted and expanded to contact the resorbable prosthesis. The balloon is then energized to heat the resorbable prosthesis to its glass transition temperature, making the resorbable prosthesis malleable. The balloon is then slowly deflated, as heat is applied to the resorbable prosthesis, so that the resorbable prosthesis remains in its glass transition state and slowly moves back to its original shape. The resorbable prosthesis will return to its original small diameter shape as the balloon deflates more and more. The decreased size of the stent then allows for removal of the stent.

The resorbable prosthesis may alternatively be inserted with, for example, positioning and heating devices as are described in U.S. Pat. No. 3,868,956, the entire contents of which are herein incorporated by reference.

A stent or prosthesis may, alternatively, comprise materials in the form of a sheet composed of thin carbon fiber threads woven in such a manner, which will permit the stent to assume the desired form and size (i.e., with the predetermined memory) upon deployment. After which the stent may easily be visualized due to the radiopacity of the carbon fiber. The stent may take the form of a typical self-expanding stent as disclosed in U.S. Pat. No. 4,655,771 which is incorporated herein by reference. Such a stent is a radially and axially flexible, elastic tubular body with a predetermined diameter that is variable under axial movement of ends of the body relative to each other and which is composed of a plurality of individually rigid but flexible and elastic thread elements defining a radially self-expanding helix. This type of stent is known in the art as a braided stent.

Placement of any of the above-described stents, to the extent practicable, may be inserted using the structures and methods of U.S. Pat. No. 4,665,771. The stent can be inserted in a body vessel in one embodiment by a device which comprises the use of a piston or, in another embodiment, by use of latch means to push the stent forward.

Any of the above-described stents, to the extent practicable, may be inserted using the structures and methods of U.S. Pat. No. 4,768,507. U.S. Pat. No. 4,768,507 discloses a stent insertion apparatus which includes an inner core member with a spiral groove formed on its outer surface, which groove cooperates with an outer sheathing to form a spiral cavity adapted to contain an expandable coil stent. The coil stent is held in a radially compressed state within the spiral cavity by exerting a radial outward force on the outer sheath. The outer surface of the inner core member is slidably mounted within the hollow outer sheath cylinder so that the spiral cavity is adapted to contain only the coil stent for which it is designed.

U.S. Pat. No. 4,743,152 discloses a device for implantation of a substantially tubular, radially expandable prosthesis including in combination the radially expandable prosthesis surrounding and concentric with a flexible probe and means for maintaining the prosthesis in a radially contracted state and for releasing the expandable prosthesis, wherein the means for maintaining and releasing the prosthesis comprises a hose concentrically surrounding the probe with one end of the hose being connected to the probe, the hose being folded inside itself, a double-walled section of the hose formed by the hose being folded inside itself, the double-walled section radially surrounding the prosthesis, a fluid-tight chamber provided between and defined by the probe and the hose, means for introducing and pressurizing a fluid in the chamber to reduce contact pressure and friction between the double-walled section of the hose, the prosthesis being released from the hose by axial relative movement of the one end of the hose with respect to an opposite end of the hose, the opposite end of the hose connected to an element of the device. The technology of this patent, to the extent practicable and compatible, can be used with any of the above-described stents and prostheses.

While preferred embodiments of the present invention have been illustrated in detail, it is apparent that modifications and adaptations of the preferred embodiment will occur to those skilled in the art. However, it is to be expressly understood that such modifications and adaptations are within the spirit and scope of the present invention as set forth in the following claims.

What is claimed is:

1. A method of inserting a prosthesis into a body passage, comprising:

providing a prosthesis in the form of a tubular body defined by a plurality of interwoven thread elements, the prosthesis possessing a memory of a predetermined configuration and having a glass transition temperature;

inserting the prosthesis into a body passage;

heating the prosthesis to a temperature at or above the glass transition temperature;

molding the prosthesis, while maintaining the prosthesis at or above the glass transition temperature, from the predetermined configuration to a larger-radius implant configuration, which is sized and shaped to conform to an internal anatomy of the body passage to expand a narrow segment of or to occlude an opening of an out pouch of the body passage;

allowing the molded prosthesis to cool to a temperature of the body passage; and after the prosthesis has cooled to a temperature of the body passage, re-heating the prosthesis to a temperature at or above the glass transition temperature.

2. The method as set forth in claim 1, wherein during re-heating of the prostheses the prosthesis is allowed to move back to the predetermined configuration under its own memory.

3. The method as set forth in claim 2, wherein the prosthesis is removed from the body passage after being allowed to move back to the predetermined configuration under its own memory.

4. The method as set forth in claim 1, wherein the tubular body includes carbon fiber.

5. The method as set forth in claim 1, wherein the prosthesis comprises polylactide.

6. The method as set forth in claim 1, wherein the prosthesis comprises at least one of a poly-lactide polymer and a copolymer of two or more poly-lactides.

7. The method as set forth in claim 1, wherein the prosthesis comprises a polymer material which is compatible with living tissue.

8. The prosthesis as set forth in claim 1, wherein the plurality of interwoven thread elements includes a first set of thread elements rotating in a first direction, and a second set of thread elements rotating in a second direction so that the first set of thread elements overlaps the second set of thread elements.

9. The method as set forth in claim 1, wherein each of the thread elements is a monofilament having the glass transition temperature.

10. The method as set forth in claim 1, wherein the tubular body comprises a braided tubular body formed from a plurality of interwoven thread elements.

11. The method as set forth in claim 10, wherein the plurality of interwoven thread elements includes a first set of thread elements oriented in a first orientation, and a second set of thread elements oriented in a second orientation that is substantially opposite to the first orientation.

12. A method of inserting a prosthesis into a body passage, comprising:

providing a prosthesis in the form of a tubular body defined by a plurality of interwoven thread elements, the prosthesis possessing a memory of a predetermined configuration and having a glass transition temperature;

inserting the prosthesis into a body passage;

heating the prosthesis to a temperature at or above the glass transition temperature;

applying an outwardly-expanding force to mold the prosthesis, while maintaining the prosthesis at or above the glass transition temperature, from the predetermined configuration to a larger-radius implant configuration, which is sized and shaped to conform to an internal anatomy of the body passage to expand a narrow segment of or to occlude an opening of an out pouch of the body passage;

allowing the molded prosthesis to cool to a temperature of the body passage; and re-heating the prosthesis to a temperature at or above the glass transition temperature, whereby the prosthesis is allowed to move back to the predetermined configuration under its own memory.

13. The method as set forth in claim 12, wherein the prosthesis comprises a polymer material which is compatible with living tissue.

14. The method as set forth in claim 12, wherein the prosthesis comprises a plastic material which is compatible with living tissue.

15. The method as set forth in claim 12, wherein the prosthesis is removed from the body passage after being allowed to move back to the predetermined configuration under its own memory.

16. A method of inserting a prosthesis into a body passage, comprising:

providing a prosthesis in the form of a tubular body defined by a plurality of interwoven thread elements, the prosthesis possessing a memory of a predetermined configuration and having a glass transition temperature;

inserting the prosthesis into a body passage;

heating the prosthesis to a temperature at or above the glass transition temperature;

molding the prosthesis, while maintaining the prosthesis at or above the glass transition temperature, from the predetermined configuration to a larger-radius implant configuration, which is sized and shaped to conform to an internal anatomy of the body passage, the molding of the prosthesis to the larger-radius implant configuration expanding a narrow segment of the body passage;

allowing the molded prosthesis to cool to a temperature of the body passage; and reheating the prosthesis to a temperature at or above the glass transition temperature.

17. The method as set forth in claim 16, wherein the prosthesis comprises polylactide.

18. The method as set forth in claim 16, wherein the prosthesis comprises at least one of a poly-lactide polymer and a copolymer of two or more poly-lactides.

19. The method as set forth in claim 16, wherein the prosthesis comprises a polymer material which is compatible with living tissue.

20. The method as set forth in claim 16, wherein the prosthesis comprises a plastic material which is compatible with living tissue.

21. The method as set forth in claim 16, wherein during re-heating of the prosthesis is allowed to move back to the predetermined configuration under its own memory.

22. The method as set forth in claim 21, wherein the prosthesis is removed from the body passage after being allowed to move back to the predetermined configuration under its own memory.

23. The method as set forth in claim 16, wherein the plurality of interwoven thread elements includes a first set of thread elements rotating in a first direction, and a second set of thread elements rotating in a second direction so that the first set of thread elements overlaps the second set of thread elements.

24. The method as set forth in claim 16, wherein each of the thread elements is a monofilament having the glass transition temperature.

25. The method as set forth in claim 16, wherein the tubular body comprises a braided tubular body formed from a plurality of interwoven thread elements.

26. The method as set forth in claim 25, wherein the plurality of interwoven thread elements includes a first set of thread elements oriented in a first orientation, and a second set of thread elements oriented in a second orientation that is substantially opposite to the first orientation.

27. A method of inserting a prosthesis into a body passage, comprising:
providing a prosthesis in the form of a tabular body including a carbon fiber and defined by a plurality of interwoven thread elements, the prosthesis possessing a memory of a predetermined configuration and having a glass transition temperature;
inserting the prosthesis into a body passage;
heating the prosthesis to a temperature at or above the glass transition temperature;
molding the prosthesis, while maintaining the prosthesis at or above the glass transition temperature, from the predetermined configuration to a larger-radius implant configuration, which is sized and shaped to conform to an internal anatomy of the body passage, the molding of the prosthesis to the larger-radius implant configuration expanding a narrow segment of the body passage; and
allowing the molded prosthesis to cool to a temperature of the body passage.

28. The method as set forth in claim 27, wherein the prosthesis comprises polylactide.

29. The method as set forth in claim 27, wherein the prosthesis comprises at least one of a poly-lactide polymer and a copolymer of two or more poly-lactides.

30. The method as set forth in claim 27, wherein the prosthesis comprises a plastic material which is compatible with living tissue.

31. The method as set forth in claim 27, wherein after the prosthesis has cooled to a temperature of the body passage the method further comprises re-heating the prosthesis to a temperature at or above the glass transition temperature.

32. The method as set forth in claim 31, wherein during re-heating of the prostheses the prosthesis is allowed to move back to the predetermined configuration under its own memory.

33. The method as set forth in claim 32, wherein the prosthesis is removed from the body passage after being allowed to move back to the predetermined configuration under its own memory.

34. The method as set forth in claim 27, wherein the plurality of interwoven thread elements includes a first set of thread elements rotating in a first direction, and a second set of thread elements rotating in a second direction so that the first set of thread elements overlaps the second set of thread elements.

35. The method as set forth in claim 27, wherein each of the thread elements is a monofilament having the glass transition temperature.

36. The method as set forth in claim 27, wherein the tubular body comprises a braided tubular body formed from a plurality of interwoven thread elements.

37. The method as set forth in claim 36, wherein the plurality of interwoven thread elements includes a first set of thread elements oriented in a first orientation, and a second set of thread elements oriented in a second orientation that is substantially opposite to the first orientation.

38. A method of inserting a prosthesis into a body passage, comprising;
providing a prosthesis in the form of a tubular body defined by a plurality of interwoven thread elements, the prosthesis possessing a memory of a predetermined configuration and having a glass transition temperature;
inserting the prosthesis into a body passage;
heating the prosthesis to a temperature at or above the glass transition temperature;
applying an outwardly-expanding force to mold the prosthesis, while maintaining the prosthesis at or above the glass transition temperature, from the predetermined configuration to a larger-radius implant configuration, which is sized and shaped to conform to an internal anatomy of the body passage to expand a narrow segment of or to occlude an opening of an out pouch of the body passage; and
allowing the molded prosthesis to cool to a temperature of the body passage, wherein after the prosthesis has cooled to a temperature of the body passage the method further comprises re-heating the prosthesis to a temperature at or above the glass transition temperature.

39. The method as set forth in claim 38, wherein the prosthesis comprises polylactide.

40. The method as set forth in claim 38, wherein the prosthesis comprises at least one of a poly-lactide polymer and a copolymer of two or more poly-lactides.

41. The method as set forth in claim 38, wherein the prosthesis comprises a polymer material which is compatible with living tissue.

42. The method as set forth in claim 38, wherein during re-heating of the prostheses the prosthesis is allowed to move back to the predetermined configuration under its own memory.

43. The method as set forth in claim 42, wherein the prosthesis is removed from the body passage after being allowed to move back to the predetermined configuration under its own memory.

44. The method as set forth in claim 38, wherein the plurality of interwoven thread elements includes a first set of thread elements rotating in a first direction, and a second set of thread elements rotating in a second direction so that the first set of thread elements overlaps the second set of thread elements.

45. The method as set forth in claim 38, wherein each of the thread elements is a monofilament having the glass transition temperature.

46. The method as set forth in claim 38, wherein the tubular body comprises a braided tubular body formed from the plurality of interwoven thread elements.

47. The method as set forth in claim 46, wherein the plurality of interwoven thread elements includes a first set of thread elements oriented in a first orientation, and a second set of thread elements oriented in a second orientation that is substantially opposite to the first orientation.

48. A method of inserting a prosthesis into a body passage, comprising:
providing a prosthesis in the form of a tubular body comprising a carbon fiber and being defined by a plurality of interwoven thread elements, the prosthesis possessing a memory of a predetermined configuration and having a glass transition temperature;

inserting the prosthesis into a body passage;

heating the prosthesis to a temperature at or above the glass transition temperature;

applying an outwardly-expanding force to mold the prosthesis, while maintaining the prosthesis at or above the glass transition temperature, from the predetermined configuration to a larger-radius implant configuration, which is sized and shaped to conform to an internal anatomy of the body passage to expand a narrow segment of or to occlude an opening of an out pouch of the body passage; and allowing the molded prosthesis to cool to a temperature of the body passage.

49. The method as set forth in claim 48, wherein the prosthesis comprises a polymer material which is compatible with living tissue.

50. The method as set forth in claim 48, wherein the prosthesis comprises a plastic material which is compatible with living tissue.

51. The method as set forth in claim 48, wherein the prosthesis comprises polylactide.

52. The method as set forth in claim 48, wherein the prosthesis comprises at least one of a poly-lactide polymer and a copolymer of two or more poly-lactides.

53. The method as set forth in claim 48, wherein:

after the prosthesis has cooled to a temperature of the body passage the method further comprises re-heating the prosthesis to a temperature at or above the glass transition temperature; and during re-heating of the prostheses the prosthesis is allowed to move back to the predetermined configuration under its own memory.

54. The method as set forth in claim 53, wherein the prosthesis is removed from the body passage after being allowed to move back to the predetermined configuration under its own memory.

55. The method as set forth in claim 48, wherein the plurality of interwoven thread elements includes a first set of thread elements rotating in a first direction and a second set of thread elements rotating in a second direction so that the first set of thread elements overlaps the second set of thread elements.

56. The method as set forth in claim 48, wherein each of the thread elements is a monofilament having the glass transition temperature.

57. The method as set forth in claim 48, wherein the tubular body comprises a braided tubular body formed from the plurality of interwoven thread elements.

58. The method as set forth in claim 57, wherein the plurality of interwoven thread elements includes a first set of thread elements oriented in a first orientation, and a second set of thread elements oriented in a second orientation that is substantially opposite to the first orientation.

* * * * *